(12) United States Patent
Wadhwa et al.

(10) Patent No.: US 7,825,220 B2
(45) Date of Patent: Nov. 2, 2010

(54) TUMOR SUPPRESSOR GENE

(75) Inventors: Renu Wadhwa, Ibaraki (JP); Takashi Sugihara, Aomori (JP); Akiko Ohide, Tokyo (JP)

(73) Assignee: Chugai Seiyaku Kabushiki Kaisha (JP)

( * ) Notice: Subject to any disclaimer, the term of this patent is extended or adjusted under 35 U.S.C. 154(b) by 0 days.

(21) Appl. No.: 12/626,290

(22) Filed: Nov. 25, 2009

(65) Prior Publication Data

US 2010/0112591 A1    May 6, 2010

Related U.S. Application Data

(60) Division of application No. 11/603,619, filed on Nov. 22, 2006, now Pat. No. 7,642,070, which is a division of application No. 10/045,815, filed on Oct. 26, 2001, now Pat. No. 7,153,935, which is a continuation-in-part of application No. PCT/JP00/02731, filed on Apr. 26, 2000.

(30) Foreign Application Priority Data

Apr. 26, 1999 (JP) ................. 11-118806

(51) Int. Cl.
C07K 16/00 (2006.01)
C12N 15/12 (2006.01)
C12N 15/00 (2006.01)

(52) U.S. Cl. ............... 530/387.1; 435/69.7; 435/7.1; 435/326; 530/388.15

(58) Field of Classification Search ............... None
See application file for complete search history.

(56) References Cited

U.S. PATENT DOCUMENTS 6,783,961 B1    8/2004  Edwards et al.

FOREIGN PATENT DOCUMENTS

WO    WO 89/04875    6/1989

OTHER PUBLICATIONS

Wassenhove-McCarthy et al., "Molecular Characterization of a Novel Basement Membrane-associated Proteoglycan, Leprecan", J. Biol. Chem.., 274:25004-25017, 1999.*
Aravind et al., "The DNA-repair protein AlkB, EGL-9, and leprecan define new families of 2-oxoglutarate- and iron-dependent dioxygenases," Genome Biol., 2:1-6 (2001).
Bowie et al., "Deciphering the Message in Protein Sequences: Tolerance to Amino Acid Substitutions," Science, 247:1306-10 (1990).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol., 111:2129-38 (1990).
Couchman et al., "Perlecan and Basement Membrane-Chondroitin Sulfate Proteoglycan (Bamacan) are Two Basement Membrane Chondroitin/Dermatan Sulfate Proteoglycans in the Englebreth-Holm-Swarm Tumor Matrix," J. Biol. Chem., 271:9595-9602 (1996).
Daigo et al., "Molecular Cloning of a Candidate Tumor Suppressor Gene, *DLC1*, from Chromosome 3p21.3," Cancer Res., 59:1966-72 (1991).
EMBL Accession No. AA887980 (Apr. 2, 1998).
Geck et al., "Early gene expression during androgen-induced inhibition of proliferation of prostate cancer cells: a new suppressor candidate on chromosome 13, in the BRCA2-Rbl locus," J. Steroid Biochem. Mol. Biol., 68:41-50 (1999).
Kaul et al., "Gros1, a potential growth suppressor on chromosome 1: its identity to basement membrane-associated proteoglycan, leprecan," Oncogene, 19:3576-83 (2000).
Lazar et al., "Transforming Growth Factor α: Mutation of Aspartic Acid 47 and Leucine 48 Results in Different Biological Activities," Mol. Cell. Biol., 8:1247-52 (1988).
Nigro et al., "The human ROX gene: Genomic structure and mutation analysis in human breast tumors," Genomics, 49:275-282 (1998).
Definition of "Polypeptide" in Merriam-Webster Online Dictionary (downloaded from url>>www.m-w.com on Aug. 21, 2004).
Roussel et al., "Inhibition of Cell Proliferation by the Mad1 Transcriptional Repressor," Mol. Cell. Biol., 16:2796-2801 (1996).
Wassenhove-McCarthy et al., "Molecular Characterization of a Novel Basement Membrane-associated Proteoglycan, Leprecan," J. Biol. Chem., 274:25004-17 (1999).
USPTO Non-Final Office Action in U.S. Appl. No. 10/045,815, mailed Aug. 24, 2004, 17 pages.
Fish & Richardson P.C., Amendment in Reply to Action dated Aug. 24, 2004 in U.S. Appl. No. 10/045,815, filed Dec. 23, 2004, 9 pages.
USPTO Final Office Action in U.S. Appl. No. 10/045,815, mailed Apr. 20, 2005, 9 pages.
Fish & Richardson, P.C., Amendment in Reply to Action dated Apr. 20, 2005 in U.S. Appl. No. 10/045,815, filed Oct. 17, 2005, 7 pages.
Fish & Richardson, P.C., Amendment in Reply to Action dated Apr. 20, 2005 in U.S. Appl. No. 10/045,815, filed May 16, 2006, 8 pages.
USPTO Non-Final Office Action in U.S. Appl. No. 11/603,619, mailed Aug. 11, 2008, 11 pages.
Fish & Richardson P.C., Amendment in Reply to Action dated Aug. 11, 2008 in U.S. Appl. No. 11/603,619, filed Nov. 12, 2008, 11 pages.
USPTO Final Office Action in U.S. Appl. No. 11/603,619, mailed Feb. 2, 2009, 9 pages.
Fish & Richardson, P.C., Amendment in Reply to Action dated Feb. 2, 2009 in U.S. Appl. No. 11/603,619, filed Jun. 2, 2009, 8 pages.
Supplemental Partial European Search Report issued in European Application No. EP00922881 on Jun. 2002 (4 pages).
International Search Report issued in PCT/JP00/02731 on Aug. 2000 (1 page).

* cited by examiner

*Primary Examiner*—Misook Yu
(74) *Attorney, Agent, or Firm*—Fish & Richardson P.C.

(57) ABSTRACT

A full-length cDNA encoding novel proteins involved in the control of cell proliferation (human Gros1-L and S) was successfully isolated from the human testis cDNA libraries. A full-length cDNA encoding the mouse homologues of the human Gros1 (mouse Gros1-L and S) was also isolated. The colony forming activity of cells exogenously expressing Gros1-L was significantly reduced, while that of cells expressing Gros1 antisense RNA was significantly increased.

15 Claims, 10 Drawing Sheets

GFPC1/7:2.8kb (83 kDa)   GFPC1/7:3.0 kb (41 kDa)

Sense (S-4)  Sense (S-8)

TUMOR SUPPRESSOR GENE

This application is a divisional of application Ser. No. 11/603,619, filed Nov. 22, 2006, which is a divisional of application Ser. No. 10/045,815, filed Oct. 26, 2001, issued as U.S. Pat. No. 7,153,935, which is a continuation-in-part of PCT Application Serial No. PCT/JP00/02731, filed Apr. 26, 2000, and claims priority to Japanese Patent Application No. 11-118806, filed Apr. 26, 1999. The disclosure of these prior applications is incorporated by reference herein.

TECHNICAL FIELD

The present invention relates to the field of biological science, more specifically to the field of cancer research. In particular, the present invention relates to novel proteins involved in the proliferation mechanism of cells. The proteins of the present invention can be used, for example, as target molecules for developing drugs against cancer.

BACKGROUND

From a cytogenetic and molecular biology perspective, there appears to be a non-random mutation on human chromosome 1p in many malignant tumors (Caron, Med. Pediatr. Oncol., 24:215-221, 1995; Schwab et al., Genes Chromosomes Cancer, 16:211-229, 1996). For example, deletions in the region of chromosome 1p have been found in various oncocytes (neuroblastomas [White et al., Eur. J. Cancer, 33:1957-1961, 1997, Gros16; Ariyama et al., Genomics, 25:114-123, 1995; Cheng et al., Oncogene, 10:291-297, 1995], meningiomas [Ishino, et al., Cancer, 83:360-366, 1998], pheochromocytomas, medullary thyroid carcinomas, neuroendocrine tumors [Moley et al., Cancer Res., 52:770-774, 1992], T cell acute lymphoblastic leukemia (T-ALL) [Iolascon et al., Leukemia, 11:359-363, 1997], colorectal cancers [Praml et al., Oncogene, 11:1357-1362, 1995, Gros13; Bomme et al., Genes Chromosomes Cancer, 21:185-194, 1998; Di Vinci et al., Cancer, 83: 415-422, 1998], mesotheliomas [Lee et al., Cancer Res., 56: 4297-4301, 1996], hepatomas [Chen et al., Cancer Genet Cytogenet, 86:102-106, 1996], endometrial carcinomas [Arlt et al., Hum. Mol. Genet, 5:1017-1021, 1996], and breast cancers [Nagai et al., Cancer Res., 55:1752-1757, 1995; Munn et al., Oncogene, 10:1653-1657, 1995]. etc.). In addition, mutations in the 1p region are thought to correlate with lymph node metastasis and tumor size [Borg et al., Genes Chromosomes Cancer, 5:311-320, 1992; Tsukamoto et al., Cancer, 82:317-322, 1998]. Moreover, the genetic mutation associated with endodermal sinus tumors (CESTs) developed in small children under four years is proposed to occur on chromosome 1p [Perlman et al., Genes Chromosomes Cancer, 16:15-20, 1996]. These facts indicate that one or more genetic mutations in chromosome 1p are associated with malignant tumors. However, the causative gene has not yet been discovered.

SUMMARY

The object of the present invention is to provide a novel protein involved in the proliferation mechanism of the cells and the gene encoding the protein, as well as methods for producing and using the same.

The present inventors screened the mouse RS-4 cell cDNA library according to the immunoscreening method using antibodies against protein p33, which is about 30 kDa in size and contained in the Triton X-100 insoluble fraction of the immortalized cell (NIH3T3) plasma membrane P100 fraction. Using thus obtained cDNA as a probe, human testis library was screened and the inventors succeeded in cloning the novel gene, Gros1, from the library. Two types of human Gros1 cDNAs (SEQ ID NOs:1 and 3) exist: one encodes a protein consisting of 363 amino acids (designated "human Gros1-S protein", SEQ ID NO:2), and the other encodes a protein consisting of 736 amino acids (designated "human Gros1-L protein", SEQ ID NO:4).

Moreover, using the cDNAs obtained by the above immunoscreening method as a probe, mouse testis library was both screened and searched for ESTs, to successfully identify mouse Gros1-L cDNA (SEQ ID NO:5) and mouse Gros1-S cDNA (SEQ ID NO:7). They encode a protein consisting of 747 amino acids (SEQ ID NO:6) and 542 amino acids (SEQ ID NO:8), respectively.

Human and mouse Gros1s were found to be homologous to the novel basement membrane-associated proteoglycan found in the data bank, leprecan, isolated from rat cDNA (Wassenhove-McCarthy et al., J. Biol. Chem., 274:25004-25017, 1999). In addition, as a result of the motif search analysis of amino acid sequences, the amino acid sequences of mouse and human Gros1-Ls were found to comprise the leucine zipper structure often observed in some members of the transcription factors.

As the result of chromosome mapping of human Gros1, the Gros1 gene was found to exist on the human chromosome 1 short arm (1p), a site suggested to have non-random mutations in many malignant tumors (Caron, Med. Pediatr. Oncol., 24:215-221, 1995; Schwab et al., Genes Chromosomes Cancer, 16:211-229, 1996).

The amount of Gros1 mRNA expressed in tissues, cells and those during developmental stages was detected by Northern blot analysis. As a result, in human, 4.4 kb and 2.5 kb bands were strongly expressed in testis, ovary and placenta, and weakly in most other tissues (FIG. 4). In addition, mRNA expression was higher in cultured human cells than in above tissues, and, in human normal cultured cells, the expression of the 2.5 kb mRNA was almost 10 times higher than that for the 4.4 kb mRNA (FIG. 5). In mouse, 3.5 kb and 2.5 kb bands were weakly expressed in most tissues, not expressed in brain or spleen; only the 2.5 kb band was expressed in the testis. Accordingly, in the testis and ovary, only the shorter form among the two transcripts of the Gros1 genes was detected. The expression during the developmental process was shown to dramatically disappear on the 11th day of the developmental process (FIG. 6).

The present inventors performed a function analysis of Gros1 by introducing the gene encoding the mouse 85 kDa protein (Gros1-L; SEQ ID NO:6) into NIH3T3 cells. As a result, cell proliferation was repressed and colony forming activity was decreased in cells expressing the full-length Gros1-L as compared to those of the control and Gros1 whose C-terminus is deleted. On the other hand, in cells in which antisense RNA of Gros1-L was expressed, the colony forming activity increased 5 folds.

Based on these analyses, Gros1 proteins are thought to be novel genes involved in the control of cell proliferation, and related to the development and growth of tumors. Thus, Gros1 proteins are useful as tools for developing pharmaceuticals against tumors.

The present invention relates to novel proteins (Gros1) involved in cell proliferation and the genes encoding them, as well as the production and the use the same. More specifically, the present invention provides the following:

1. A DNA of any one of the following (a) to (d):
   (a) a DNA encoding the protein consisting of the amino acid sequence of any one of SEQ ID NOs:2, 4, 6, or 8;
   (b) a DNA containing the coding region of the nucleotide sequence of any one of SEQ ID NOs:1, 3, 5, or 7;
   (c) a DNA encoding a protein consisting of the amino acid sequence of any one of SEQ ID NOs:2, 4, 6, or 8, in which one or more amino acids are replaced, deleted, inserted, and/or added, the encoded protein being functionally equivalent to the protein consisting of the amino acid sequence of any one of SEQ ID NOs:2, 4, 6, or 8; and
   (d) a DNA hybridizing under stringent conditions with a DNA consisting of the nucleotide sequence of any one of SEQ ID NOs:1, 3, 5, or 7, and encoding a protein functionally equivalent to the protein consisting of the amino acid sequence of any one of SEQ ID NOs:2, 4, 6, or 8.

2. A DNA encoding a partial peptide of the protein consisting of the amino acid sequence of any one of SEQ ID NOs:2, 4, 6, or 8.

3. A vector into which the DNA of (1) or (2) is inserted.

4. A transformed cell harboring the DNA of (1) or (2), or the vector of (3).

5. A protein or peptide encoded by the DNA of (1) or (2).

6. A method for producing the protein or peptide of (5), comprising the steps of culturing the transformed cell of (4), and collecting the protein expressed from the cells or the culture supernatant thereof.

7. An antibody binding to the protein of (5).

8. A polynucleotide hybridizing with the DNA consisting of the nucleotide sequence of any one of SEQ ID NOs:1, 3, 5, or 7 or the complementary strand thereof, and comprising at least 15 nucleotides.

9. A method of screening for a compound that binds to the protein of (5), comprising the steps of
   (a) contacting a subject sample with the protein or the partial peptide thereof;
   (b) detecting the binding activity of the subject sample with the protein or the partial peptide thereof; and
   (c) selecting the test compound that binds to the protein or the partial peptide thereof.

10. A compound binding to the protein of (5), which can be isolated by the method of (9).

11. A method of screening for a compound that promotes or inhibits the activity of the protein of (5), comprising the steps of:
    (a) culturing cells which express the protein or the partial peptide thereof in the presence of a subject sample;
    (b) detecting the proliferation of the cell; and
    (c) selecting the compound that promotes or inhibits the proliferation as compared to the proliferation detected in the absence of the subject sample.

12. A compound that promotes or inhibits the activity of the protein of (5), which can be isolated by the method of (11).

The present invention provides a novel protein Gros1 involved in the cell proliferation mechanism. SEQ ID NOs:1 and 3 show nucleotide sequences of the cDNA of two types of human Gros1 (human Gros1-S and human Gros1-L, respectively) isolated by the inventors, and SEQ ID NOs:2 and 4 show the amino acids sequences encoded by the cDNAs, respectively. SEQ ID NOs:5 and 7 show nucleotide sequences of the cDNA of two types of mouse Gros1 (mouse Gros1-L and mouse Gros1-S, respectively) isolated by the present inventors, and SEQ ID NOs:6 and 8 show the amino acids sequences encoded by the cDNAs, respectively.

When the Gros1-L protein was expressed exogenously in NIH-3T3 cells, cell proliferation was inhibited and the colony forming activity decreased. In contrast, when the expression of Gros1-L protein was repressed by the introduction of Gros1 antisense cDNA in NIH-3T3 cells, the colony forming activity increased dramatically. Thus, the Gros1 protein is considered to be involved in the control of cell proliferation. This is also supported by the fact that human Gros1 gene is present on chromosome 1 short arm (1p), a site that is purportedly associated with malignant tumors. Therefore, the Gros1 proteins of the present invention can be conveniently used as tools, for purifying or cloning factors controlling cell proliferation, as well as targets, for example, for screening candidate compounds of drugs useful for treating or preventing disorders related to cell proliferation, such as tumors. Moreover, the Gros1 genes can be applied in the treatment, for example, gene therapy for various tumors.

The present invention encompasses proteins functionally equivalent to the Gros1 proteins. Such proteins include, for example, homologous proteins of other organisms corresponding to the human or mouse Gros1 protein, as well as mutants of human or mouse Gros1 proteins.

In the present invention, the term "functionally equivalent" means that the subject protein has the activity to inhibit cell proliferation like Gros1 proteins. Whether the subject protein has a cell proliferation inhibitory activity or not can be judged by introducing the DNA encoding the subject protein into a cell, such as NIH-3T3, expressing the protein, and detecting repression of proliferation of the cells or reduction in colony forming activity.

Methods for preparing proteins functionally equivalent to a given protein are well known by a person skilled in the art and include known methods of introducing mutations into the protein. For example, one skilled in the art can prepare proteins functionally equivalent to the human or mouse Gros1 protein by introducing an appropriate mutation in the amino acid sequence of the human or mouse Gros1 protein by site-directed mutagenesis (Hashimoto-Gotoh et al., Gene, 152: 271-275, 1995; Zoller et al., Methods Enzymol., 100:468-500, 1983; Kramer et al., Nucleic Acids Res., 12:9441-9456, 1984; Kramer et al., Methods Enzymol., 154:350-367, 1987; Kunkel, Proc. Natl. Acad. Sci. USA, 82:488-492, 1985; Kunkel, Methods Enzymol., 85:2763-2766, 1988). Amino acid mutations can occur in nature, too. The protein of the present invention includes those proteins having the amino acid sequences of the human or mouse Gros1 protein in which one or more amino acids are mutated, provided the resulting mutated proteins are functionally equivalent to the human or mouse Gros1 protein. The number of amino acids to be mutated in such a mutant is generally 10 amino acids or less, preferably 6 amino acids or less, and more preferably 3 amino acids or less.

Mutated or modified proteins, proteins having amino acid sequences modified by deleting, adding and/or replacing one or more amino acid residues of a certain amino acid sequence, have been known to retain the original biological activity (Mark et al., Proc. Natl. Acad. Sci. USA, 81:5662-5666, 1984; Zoller et al., Nucleic Acids Res., 10:6487-6500, 1982; Wang et al., Science, 224:1431-1433; Dalbadie-McFarland et al., Proc. Natl. Acad. Sci. USA, 79:6409-6413, 1982).

The amino acid residue to be mutated is preferably mutated into a different amino acid in which the properties of the amino acid side-chain are conserved. Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). (The parenthetic letters indicate the one-letter codes of amino acids).

An example of a protein to which one or more amino acids residues are added to the amino acid sequence of human or mouse Gros1 protein (SEQ ID NOs:2, 4, 6, or 8) is a fusion protein containing the human or mouse Gros1 protein. Fusion proteins are, fusions of the human or mouse Gros1 protein and other peptides or proteins, and are included in the present invention. Fusion proteins can be made by techniques well known to a person skilled in the art, such as by linking the DNA encoding the human or mouse Gros1 protein of the invention with DNA encoding other peptides or proteins, so that the frames match, inserting the fusion DNA into an expression vector and expressing it in a host. There is no restriction as to the peptides or proteins fused to the protein of the present invention.

Known peptides that can be used as peptides that are fused to the protein of the present invention include, for example, FLAG (Hopp et al., Biotechnology, 6:1204-1210, 1988), 6×His containing six His (histidine) residues, 10×His, HA (Influenza agglutinin), human c-myc fragment, VSP-GP fragment, p18HIV fragment, T7-tag, HSV-tag, E-tag, SV40T antigen fragment, lck tag, α-tubulin fragment, B-tag, Protein C fragment, and the like. Examples of proteins that may be fused to a protein of the invention include GST (glutathione-S-transferase), HA (Influenza agglutinin), immunoglobulin constant region, β-galactosidase, MBP (maltose-binding protein), and such.

Fusion proteins can be prepared by fusing commercially available DNA, encoding the fusion peptides or proteins discussed above, with the DNA encoding the protein of the present invention and expressing the fused DNA prepared.

An alternative method known in the art to isolate functionally equivalent proteins is, for example, the method using a hybridization technique (Sambrook et al., Molecular Cloning 2nd ed. 9.47-9.58, Cold Spring Harbor Lab. Press, 1989). One skilled in the art can readily isolate a DNA having high homology with a whole or part of the DNA sequence (SEQ ID NOs:1, 3, 5 or 7) encoding the human or mouse Gros1 protein, and isolate functionally equivalent proteins to the human or mouse Gros1 protein from the isolated DNA. The proteins of the present invention include those that are encoded by DNA that hybridize with a whole or part of the DNA sequence encoding the human or mouse Gros1 protein and are functionally equivalent to the human or mouse Gros1 protein. These proteins include mammal homologues corresponding to the protein derived from human or mouse (for example, a protein encoded by a monkey, rat, rabbit and bovine gene). In isolating a cDNA highly homologous to the DNA encoding the human or mouse Gros1 protein from animals, it is particularly preferable to use tissues from ovary or testis.

The condition of hybridization for isolating a DNA encoding a protein functionally equivalent to the human or mouse Gros1 protein can be routinely selected by a person skilled in the art. For example, hybridization may be performed by conducting prehybridization at 68° C. for 30 min or longer using "Rapid-hyb buffer" (Amersham LIFE SCIENCE), adding a labeled probe, and warming at 68° C. for 1 hour or longer. The following washing step can be conducted, for example, in a low stringent condition. A low stringent condition is, for example, 42° C., 2×SSC, 0.1% SDS, or preferably 50° C., 2×SSC, 0.1% SDS. More preferably, high stringent conditions are used. A high stringent condition is, for example, washing 3 times in 2×SSC, 0.01% SDS at room temperature for 20 min, then washing 3 times in 1×SSC, 0.1% SDS at 37° C. for 20 min, and washing twice in 1×SSC, 0.1% SDS at 50° C. for 20 min. However, several factors such as temperature and salt concentration can influence the stringency of hybridization and one skilled in the art can suitably select the factors to achieve the requisite stringency.

In place of hybridization, a gene amplification method, for example, the polymerase chain reaction (PCR) method, can be utilized to isolate a DNA encoding a protein functionally equivalent to the human or mouse Gros1 protein, using a primer synthesized based on the sequence information of the DNA (SEQ ID NO:1, 3, 5 or 7) encoding the human or mouse Gros1 protein.

Proteins that are functionally equivalent to the human or mouse Gros1 protein encoded by the DNA isolated through the above hybridization techniques or gene amplification techniques, normally have a high homology to the amino acid sequence of the human or mouse Gros1 protein. "High homology" typically refers to a homology of 40% or higher, preferably 60% or higher, more preferably 80% or higher, even more preferably 95% or higher. The homology of a protein can be determined by following the algorithm in "Wilbur, W. J. and Lipman, D. J. Proc. Natl. Acad. Sci. USA (1983) 80, 726-730".

A protein of the present invention may have variations in amino acid sequence, molecular weight, isoelectric point, the presence or absence of sugar chains, or form, depending on the cell or host used to produce it or the purification method utilized. Nevertheless, so long as it has a function equivalent to that of the human or mouse Gros1 protein (SEQ ID NO:2, 4, 6 or 8) of the present invention, it is within the scope of the present invention.

The term "substantially pure" as used herein in reference to a given polypeptide means that the polypeptide is substantially free from other biological macromolecules. For example, the substantially pure polypeptide is at least 75%, 80, 85, 95, or 99% pure by dry weight. Purity can be measured by any appropriate standard method known in the art, for example, by column chromatography, polyacrylamide gel electrophoresis, or HPLC analysis.

Accordingly, the invention includes a polypeptide having a sequence shown as SEQ ID NO:2, 4, 6 or 8. The invention also includes a polypeptide, or fragment thereof, that differs from the corresponding sequence shown as SEQ ID NO:2, 4, 6 or 8. The differences are, preferably, differences or changes at a non-essential residue or a conservative substitution. In one embodiment, the polypeptide includes an amino acid sequence at least about 60% identical to a sequence shown as SEQ ID NO:2, 4, 6 or 8, or a fragment thereof. Preferably, the polypeptide is at least 65%, 70%, 75%, 80%, 85%, 90%, 95%, 98%, 99% or more identical to SEQ ID NO:2, 4, 6 or 8 and has at least one cell proliferation related function or activity described herein, e.g., the polypeptide inhibits cell proliferation or decreases colony forming activity. Preferred polypeptide fragments of the invention are at least 10%, preferably at least 20%, 30%, 40%, 50%, 60%, 70%, or more, of the length of the sequence shown as SEQ ID NO:2, 4, 6 or 8 and have at least one cell proliferation related function or activity described herein. Or alternatively, the fragment can be merely an immunogenic fragment.

The proteins of the present invention can be prepared as recombinant proteins or natural proteins, by methods well known to those skilled in the art. A recombinant protein can be prepared by inserting a DNA, which encodes the protein of the present invention (for example, the DNA comprising the nucleotide sequence of SEQ ID NOs:1, 3, 5, or 7), into an appropriate expression vector, introducing the vector into an appropriate host cell, collecting thus obtained recombinants, obtaining the extract thereof, and purifying the protein by subjecting the extract to chromatography, for example, ion exchange chromatography, reverse phase chromatography, gel filtration, or affinity chromatography utilizing a column to which antibodies against the protein of the present invention is fixed, or by combining more than one of aforementioned columns.

Also when the protein of the present invention is expressed within host cells (for example, animal cells and E. coli) as a fusion protein with glutathione-S-transferase protein or as a recombinant protein supplemented with multiple histidines, the expressed recombinant protein can be purified using a glutathione column or nickel column.

After purifying the fusion protein, it is also possible to exclude regions other than the objective protein by cutting with thrombin or factor-Xa as required.

A natural protein can be isolated by methods known to a person skilled in the art, for example, by contacting the affinity column, in which antibodies binding to the Gros1 protein described below are bound, with the extract of tissues or cells expressing the protein of the present invention. The antibodies can be polyclonal antibodies or a monoclonal antibodies.

The present invention also encompasses partial peptides of the protein of the present invention. The partial peptide has an amino acid sequence specific to the protein of the present invention and consists of at least 7 amino acids, preferably 8 amino acids or more, and more preferably 9 amino acids or more. The partial peptide can be used, for example, for preparing antibodies against the protein of the present invention, screening for a compound that binds to the protein of the present invention, and screening for accelerators or inhibitors of the protein of the present invention.

A partial peptide of the invention can be produced by genetic engineering, by known methods of peptide synthesis, or by digesting the protein of the invention with an appropriate peptidase. For peptide synthesis, for example, solid phase synthesis or liquid phase synthesis may be used.

Furthermore, the present invention provides DNA encoding the proteins of the present invention. The DNA of the present invention can be used for the in vivo or in vitro production of the protein of the present invention as described above, or can be applied to gene therapy for diseases attributed to genetic abnormality in the gene encoding the protein of the present invention. Any form of the DNA of the present invention can be used, so long as it encodes the protein of the present invention. Specifically, cDNA synthesized from the mRNA, genomic DNA, and chemically synthesized DNA can be used. The DNA of the present invention include a DNA comprising a given nucleotide sequences as well as its degenerate sequences, so long as the resulting DNA encodes a protein of the present invention.

The DNA of the present invention can be prepared by methods known to a person skilled in the art. For example, the DNA of the present invention can be prepared by: preparing a cDNA library from cells which express the protein of the present invention, and conducting hybridization using a partial sequence of the DNA of the present invention (for example, SEQ ID NOs:1, 3, 5, or 7) as a probe. A cDNA library can be prepared, for example, by the method described in Sambrook et al., Molecular Cloning, Cold Spring Harbor Laboratory Press (1989); alternatively, commercially available cDNA libraries may be used. A cDNA library can be also prepared by: extracting RNAs from cells expressing the protein of the present invention, synthesizing oligo DNAs based on the sequence of the DNA of the present invention (for example, SEQ ID NOs:1, 3, 5 or 7), conducting PCR by using the oligos as primers, and amplifying cDNAs encoding the protein of the present invention.

As used herein, an "isolated nucleic acid" is a nucleic acid, the structure of which is not identical to that of any naturally occurring nucleic acid or to that of any fragment of a naturally occurring genomic nucleic acid spanning more than three genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in random, uncharacterized mixtures of different DNA molecules, transfected cells, or cell clones, e.g., as these occur in a DNA library such as a cDNA or genomic DNA library.

Accordingly, in one aspect, the invention provides an isolated or purified nucleic acid molecule that encodes a polypeptide described herein or a fragment thereof. Preferably, the isolated nucleic acid molecule includes a nucleotide sequence that is at least 60% identical to the nucleotide sequence shown in SEQ ID NO:1, 3, 5 or 7. More preferably, the isolated nucleic acid molecule is at least 65%, 70%, 75%, 80%, 85%, 90%, 91%, 92%, 93%, 94%, 95%, 96%, 97%, 98%, 99%, or more, identical to the nucleotide sequence shown in SEQ ID NO:1, 3, 5 or 7. In the case of an isolated nucleic acid molecule which is longer than or equivalent in length to the reference sequence, e.g., SEQ ID NO:1, 3, 5 or 7, the comparison is made with the full length of the reference sequence. Where the isolated nucleic acid molecule is shorter that the reference sequence, e.g., shorter than SEQ ID NO:1, 3, 5 or 7, the comparison is made to a segment of the reference sequence of the same length (excluding any loop required by the homology calculation).

As used herein, "% identity" of two amino acid sequences, or of two nucleic acid sequences, is determined using the algorithm of Karlin and Altschul (Proc. Natl. Acad. Sci. USA, 87:2264-2268, 1990), modified as in Karlin and Altschul, Proc. Natl. Acad. Sci. USA, 90:5873-5877, 1993)). Such an algorithm is incorporated into the NBLAST and XBLAST programs of Altschul et al. (J. Mol. Biol., 215:403-410, 1990). BLAST nucleotide searches are performed with the NBLAST program, score=100, wordlength=12. BLAST protein searches are performed with the NBLAST program, score=50, wordlength=3. To obtain gapped alignment for comparison purposes GappedBLAST is utilized as described in Altschul et al. (Nucleic Acids Res., 25:3389-3402, 1997). When utilizing BLAST and GappedBLAST programs the default parameters of the respective programs (e.g., XBLAST and NBLAST) are used to obtain nucleotide sequences homologous to a nucleic acid molecule of the invention.

In addition, by sequencing the nucleotides of the obtained cDNA, the translation region encoded by the cDNA can be determined, and the amino acid sequence of the protein of the present invention can be obtained. Moreover, by screening the genomic DNA library using the obtained cDNA as a probe, the genomic DNA can be isolated.

More specifically, mRNAs may first be prepared from cells, tissue, or organ (for example, ovary, testis, placenta, etc.) in which the protein of the invention is expressed.

Known methods can be used to isolate mRNAs; for instance, total RNA may be prepared by guanidine ultracentrifugation (Chirgwin et al., Biochemistry, 18:5294-5299, 1979) or AGPC method (Chomczynski et al., Anal. Biochem., 162: 156-159, 1987). In addition, mRNA may be purified from total RNA using mRNA Purification Kit (Pharmacia) and such or, alternatively, mRNA may be directly purified by QuickPrep mRNA Purification Kit (Pharmacia).

The obtained mRNA is used to synthesize cDNA using reverse transcriptase. cDNA may be synthesized by using a commercially available kit, such as the AMV Reverse Transcriptase First-strand cDNA Synthesis Kit (Seikagaku Kogyo). Alternatively, cDNA may be synthesized and amplified following the 5'-RACE method (Frohman et al., Proc. Natl. Acad. Sci. USA, 85:8998-9002, 1988; Belyaysky et al., Nucleic Acids Res., 17:2919-2932, 1989), which uses a primer and such, described herein, the 5'-Ampli FINDER RACE Kit (Clontech), and polymerase chain reaction (PCR).

A desired DNA fragment is prepared from the PCR products and ligated with a vector DNA. The recombinant vectors are used to transform E. coli and such, and a desired recombinant vector is prepared from a selected colony. The nucleotide sequence of the desired DNA can be verified by conventional methods, such as dideoxynucleotide chain termination.

The nucleotide sequence of a DNA of the invention may be designed to be expressed more efficiently by taking into account the frequency of codon usage in the host to be used for expression (Grantham et al., Nucleic Acids Res., 9:43-74, 1981). The DNA of the present invention may be altered by a commercially available kit or a conventional method. For instance, the DNA may be altered by digestion with restriction enzymes, insertion of a synthetic oligonucleotide or an appropriate DNA fragment, addition of a linker, or insertion of the initiation codon (ATG) and/or the stop codon (TAA, TGA, or TAG).

Specifically, the DNA of the present invention encompasses the DNA comprising the nucleotide sequence from base A at position 52 to base C at position 1140 of SEQ ID NO:1; the DNA from base A at position 52 to base A at position 2259 of SEQ ID NO:3; the DNA from base A at position 12 to base G at position 2252 of SEQ ID NO:5; and that from base A at position 12 to base A at position 1640 of SEQ ID NO:3.

Furthermore, the present invention provides a DNA that hybridizes under stringent conditions with a DNA having a nucleotide sequence of SEQ ID NOs:1, 3, 5 or 7, and encodes a protein functionally equivalent to the protein of the invention described above.

One skilled in the art may appropriately choose stringent conditions. For example, low stringent condition can be used. More preferably, high stringent condition can be used. These conditions are the same as those described above. The hybridizing DNA above is preferably a cDNA or a chromosomal DNA.

The present invention also provides a vector into which a DNA of the present invention is inserted. A vector of the present invention is useful to keep a DNA of the present invention in host cell, or to express the protein of the present invention.

When E. coli is a host cell and the vector is amplified and produced in a large amount in E. coli (e.g., JM109, DH5α, HB101, or XL1Blue), the vector should have "ori" to be amplified in E. coli and a marker gene for selecting transformed E. coli (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc., can be used. In addition, pGEM-T, pDIRECT, and pT7 can also be used for subcloning and extracting cDNA as well as the vectors described above. When a vector is used to produce the protein of the present invention, an expression vector is especially useful. For example, an expression vector to be expressed in E. coli should have the above characteristics to be amplified in E. coli. When E. coli, such as JM109, DH5α, HB101, or XL1 Blue, are used as a host cell, the vector should have a promoter, for example, lacZ promoter (Ward et al., Nature, 341: 544-546, 1989; FASEB J, 6:2422-2427, 1992), araB promoter (Better et al., Science, 240:1041-1043, 1988), or T7 promoter or the like, that can efficiently express the desired gene in E. coli. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors.

Additionally, the vector may also contain a signal sequence for polypeptide secretion. An exemplary signal sequence that directs the protein to be secreted to the periplasm of the E. coli is the pelB signal sequence (Lei et al., J. Bacteriol., 169: 4379, 1987). Means for introducing the vectors into the target host cells include, for example, the calcium chloride method, and the electroporation method.

In addition to E. coli, for example, expression vectors derived from mammals (for example, pcDNA3 (Invitrogen) and pEGF-BOS (Nucleic Acids. Res., 18(17):5322, 1990), pEF, pCDM8), expression vectors derived from insect cells (for example, "Bac-to-BAC baculovirus expression system" (GIBCO BRL), pBacPAK8), expression vectors derived from plants (for example pMH1, pMH2), expression vectors derived from animal viruses (for example, pHSV, pMV, pAdexLcw), expression vectors derived from retroviruses (for example, pZIpneo), expression vector derived from yeast (for example, "*Pichia* Expression Kit" (Invitrogen), pNV11, SP-Q01), and expression vectors derived from *Bacillus subtilis* (for example, pPL608, pKTH50) can be used for producing the protein of the present invention.

In order to express the vector in animal cells, such as CHO, COS, or NIH3T3 cells, the vector should have a promoter necessary for expression in such cells, for example, the SV40 promoter (Mulligan et al., Nature (1979) 277, 108), the MMLV-LTR promoter, the EF1a promoter (Mizushima et al., Nucleic Acids Res. (1990) 18, 5322), the CMV promoter, and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV, and pOP13.

In addition, methods may be used to express a gene stably and, at the same time, to amplify the copy number of the gene in cells. For example, a vector comprising the complementary DHFR gene (for example pCHO I) may be introduced into CHO cells in which the nucleic acid synthesizing pathway is deleted, and then amplified by methotrexate (MTX). Furthermore, in case of transient expression of a gene, the method wherein a vector comprising a replication origin of SV40 (pcD, etc.) is transfected into COS cells comprising the SV40 T antigen expressing gene on the chromosome can be used.

The DNA of the present invention can further be expressed in vivo in animals, for example, by inserting the DNA of the present invention into an appropriate vector and introducing it into living bodies by methods such as the retrovirus method, the liposome method, the cationic liposome method, and the adenovirus method. In such a manner, gene therapy against diseases attributed to mutation of Gros1 gene of the present invention can be accomplished. As a vector to be used, for example, adenovirus vector (for example pAdexlcw), and retrovirus vector (for example, pZIPneo) can be mentioned, but is not restricted thereto. General gene manipulation, such as insertion of the DNA of the present invention to a vector, can be performed according to conventional methods (Molecular Cloning, 5:61-65. 63). Administration into a living body can be either an ex vivo method, or in vivo method.

The present invention further provides a host cell into which the vector of the present invention has been transfected. The host cell into which the vector of the invention is transfected is not particularly limited. For example, $E.$ $coli$, various animal cells and such can be used. The host cells of the present invention can be used, for example, as a production system for producing or expressing the protein of the present invention. The present invention provides methods of producing a protein of the invention both in vitro and in vivo. For in vitro production, eukaryotic cells or prokaryotic cells can be used as host cells.

Useful eukaryotic cells may be animal, plant, or fungi cells. Exemplary animal cells include, for example, mammalian cells such as CHO (J. Exp. Med., 108:945, 1995), COS, 3T3, myeloma, baby hamster kidney (BHK), HeLa, or Vero cells, amphibian cells such as Xenopus oocytes (Valle et al., Nature, 291:340-358, 1981), or insect cells such as sf9, sf21, or Tn5 cells. CHO cells lacking DHFR gene (dhfr-CHO) (Proc. Natl. Acad. Sci. USA, 77:4216-4220, 1980) or CHO K-1 (Proc. Natl. Acad. Sci. USA, 60:1275, 1968) may also be used. Of the animal cells, CHO cells are particularly preferable for the mass expression. A vector can be transfected into host cells by, for example, the calcium phosphate method, the DEAE-dextran method, the cationic liposome DOTAP (Boehringer Mannheim), the electroporation method, the lipofection method, and so on.

As plant cells, plant cells originating from $Nicotiana$ $tabacum$ are known as protein-production systems, and may be used as callus cultures. As fungi cells, yeast cells such as $Saccharomyces$, including $Saccharomyces$ $cerevisiae$, or filamentous fungi such as $Aspergillus$, including $Aspergillus$ $niger$, are known and may be used herein. Useful prokaryotic cells include bacterial cells, such as $E.$ $coli$, for example, JM109, DH5α, and HB101. Other bacterial systems include, $Bacillus$ $subtilis$.

These cells are transformed by a desired DNA, and the resulting transformants are cultured in vitro to obtain the protein. Transformants can be cultured using known methods. Culture medium for animal cells include, for example, DMEM, MEM, RPMI1640, or IMDM may be used with or without serum supplement such as fetal calf serum (FCS). The pH of the culture medium is preferably between about 6 and 8. Such cells are typically cultured at about 30 to 40° C. for about 15 to 200 hr, and the culture medium may be replaced, aerated, or stirred if necessary.

Animal and plant hosts may be used for in vivo production. For example, a desired DNA can be transfected into an animal or plant host. Encoded proteins are produced in vivo, and then recovered. These animal and plant hosts are included in host cells of the present invention.

Animals to be used for the production system described above include, but are not limited to, mammals and insects. Mammals, such as goat, porcine, sheep, mouse, and bovine, may be used (Vicki Glaser, SPECTRUM Biotechnology Applications (1993)). Alternatively, the mammals may be transgenic animals.

For instance, a desired DNA may be prepared as a fusion gene, by fusing it with a gene, such as goat β casein gene which encodes a protein specifically produced into milk. DNA fragments comprising the fusion gene are injected into goat embryos, which are then impregnated into female goats. Proteins are recovered from milk produced by the transgenic goats (i.e., those born from the goats that had received the modified embryos) or from their offspring. To increase the amount of milk containing the proteins produced by transgenic goats, appropriate hormones may be administered to them (Ebert et al., Bio/Technology, 12:699-702, 1994).

Alternatively, insects, such as the silkworm, may be used. A DNA encoding a desired protein inserted into baculovirus can be used to transfect silkworms, and the desired protein may be recovered from their body fluid (Susumu et al., Nature, 315:592-594, 1985).

As plants, for example, tobacco can be used. In use of tobacco, a DNA encoding a desired protein may be inserted into a plant expression vector, such as pMON530, which is introduced into bacteria, such as $Agrobacterium$ $tumefaciens$. Then, the bacteria is used to transfect a tobacco plant, such as $Nicotiana$ $tabacum$, and a desired polypeptide is recovered from their leaves (Julian et al., Eur. J. Immunol., 24:131-138, 1994).

A protein of the present invention obtained as above may be isolated from inside or outside (such as medium) of host cells, and purified as a substantially pure homogeneous protein. The method for protein isolation and purification is not limited to any specific method; in fact, any standard method may be used. For instance, column chromatography, filter, ultrafiltration, salt precipitation, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the protein.

Examples of chromatography include, for example, affinity chromatography, ion-exchange chromatography, hydrophobic chromatography, gel filtration, reverse phase chromatography, adsorption chromatography, and such (Strategies for Protein Purification and Characterization: A Laboratory Course Manual. Ed. Daniel R. Marshak et al., Cold Spring Harbor Laboratory Press (1996)). These chromatographies may be performed by liquid chromatography, such as HPLC and FPLC. Thus, the present invention provides for highly purified proteins prepared by the above methods.

A protein of the present invention may be optionally modified or partially deleted by treating it with an appropriate protein modification enzyme before or after purification. Useful protein modification enzymes include, but are not limited to, trypsin, chymotrypsin, lysylendopeptidase, protein kinase, glucosidase and so on.

The present invention provides an antibody that binds to the protein of the invention. The antibody of the invention can be used in any form, such as monoclonal or polyclonal antibodies, and includes antiserum obtained by immunizing an animal such as a rabbit with the protein of the invention, all classes of polyclonal and monoclonal antibodies, human antibodies, and humanized antibodies produced by genetic recombination.

A protein of the invention used as an antigen to obtain an antibody may be derived from any animal species, but preferably is derived from a mammal such as a human, mouse, or rat, more preferably from a human. A human-derived protein may be obtained from the nucleotide or amino acid sequences disclosed herein.

According to the present invention, the protein to be used as an immunization antigen may be a complete protein or a partial peptide of the protein. A partial peptide may comprise, for example, the amino (N)-terminal or carboxy (C)-terminal fragment of a protein of the present invention. Herein, an antibody is defined as a protein that reacts with either the full length or a fragment of a protein of the present invention.

A gene encoding a protein of the invention or its fragment may be inserted into a known expression vector, which is then used to transform a host cell as described herein. The desired protein or its fragment may be recovered from the outside or inside of host cells by any standard method, and may subsequently be used as an antigen. Alternatively, cells expressing the protein or their lysates, or a chemically synthesized protein may be used as the antigen.

Any mammalian animal may be immunized with the antigen, but preferably the compatibility with parental cells used for cell fusion is taken into account. In general, animals of Rodentia, Lagomorpha, or Primates are used.

Animals of Rodentia include, for example, mouse, rat, and hamster. Animals of Lagomorpha include, for example, rabbit. Animals of Primates include, for example, a monkey of Catarrhini (old world monkey) such as *Macaca fascicularis*, rhesus monkey, sacred baboon, and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion, and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum is examined by a standard method for an increase in the amount of desired antibodies.

Polyclonal antibodies against the proteins of the present invention may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum. Immunoglobulin G or M can be prepared from a fraction which recognizes only the protein of the present invention using, for example, an affinity column coupled with the protein of the present invention, and further purifying this fraction by using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre et al., Methods Enzymol., 73:3-46, 1981).

Resulting hybridomas obtained by the cell fusion may be selected by cultivating them in a standard selection medium, such as HAT medium (hypoxanthine, aminopterin, and thymidine containing medium). The cell culture is typically continued in the HAT medium for several days to several weeks, the time being sufficient to allow all the other cells, with the exception of the desired hybridoma (non-fused cells), to die. Then, the standard limiting dilution is performed to screen and clone a hybridoma cell producing the desired antibody.

In addition to the above method in which a non-human animal is immunized with an antigen for preparing hybridoma, a hybridoma producing a desired human antibody that is able to bind to the protein can be obtained by the following method. First, human lymphocytes such as those infected by EB virus may be immunized with a protein, protein expressing cells, or their lysates in vitro. Then, the immunized lymphocytes are fused with human-derived myeloma cells that are capable of indefinitely dividing, such as U266, to yield the desired hybridoma (Unexamined Published Japanese Patent Application No. (JP-A) Sho 63-17688).

The obtained hybridomas are subsequently transplanted into the abdominal cavity of a mouse and the ascites are harvested. The obtained monoclonal antibodies can be purified by, for example, ammonium sulfate precipitation, a protein A or protein G column, DEAE ion exchange chromatography, or an affinity column to which the protein of the present invention is coupled. The antibody of the present invention can be used not only for purification and detection of the protein of the present invention, but also as a candidate for agonists and antagonists of the protein of the present invention. In addition, this antibody can be applied to the antibody treatment for diseases related to the protein of the present invention. When the obtained antibody is to be administered to the human body (antibody treatment), a human antibody or a humanized antibody is preferable for reducing immunogenicity.

For example, transgenic animals having a repertory of human antibody genes may be immunized with an antigen selected from a protein, protein expressing cells, or their lysates. Antibody producing cells are then collected from the animals and fused with myeloma cells to obtain hybridoma, from which human antibodies against the protein can be prepared (see WO92-03918, WO93-2227, WO94-02602, WO94-25585, WO96-33735, and WO96-34096).

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck C. A. K. and Larrick J. W. Therapeutic Monoclonal Antibodies, published in the United Kingdom by MacMillan Publishers LTD (1990)). A DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the proteins of the invention. For instance, the antibody fragment may be Fab, F(ab')$_2$, Fv, or single chain Fv (scFv), in which Fv fragments from H and L chains are ligated by an appropriate linker (Huston et al., Proc. Natl. Acad. Sci. USA, 85:5879-5883, 1988). More specifically, an antibody fragment may be generated by treating an antibody with an enzyme, such as papain or pepsin. Alternatively, a gene encoding the antibody fragment may be constructed, inserted into an expression vector, and expressed in an appropriate host cell (see, for example, Co et al., J. Immunol., 152:2968-2976, 1994; Better et al., Methods Enzymol., 178:476-496, 1989; Pluckthun et al., Methods Enzymol., 178:497-515, 1989; Lamoyi, Methods Enzymol., 121:652-

663, 1986; Rousseaux et al., Methods Enzymol., 121:663-669, 1986; Bird et al., Trends Biotechnol., 9:132-137, 1991).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, comprising the complementarity determining region (CDR) derived from nonhuman antibody, the frame work region (FR) derived from human antibody, and the constant region. Such antibodies can be prepared by using known technology.

Antibodies obtained as above may be purified to homogeneity. For example, the separation and purification of the antibody can be performed according to separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis, isoelectric focusing, and others (Antibodies: A Laboratory Manual. Ed Harlow and David Lane, Cold Spring Harbor Laboratory, 1988), but are not limited thereto.

A protein A column and protein G column can be used as the affinity column. Exemplary protein A columns to be used include, for example, Hyper D, POROS, and Sepharose F.F. (Pharmacia).

Exemplary chromatography, with the exception of affinity includes, for example, ion-exchange chromatography, hydrophobic chromatography, gel filtration, reverse-phase chromatography, adsorption chromatography, and the like (Strategies for Protein Purification and Characterization: A Laboratory Course Manual. Ed Daniel R. Marshak et al., Cold Spring Harbor Laboratory Press, 1996). The chromatographic procedures can be carried out by liquid-phase chromatography, such as HPLC, FPLC.

For example, measurement of absorbance, enzyme-linked immunosorbent assay (ELISA), enzyme immunoassay (EIA), radioimmunoassay (RIA), and/or immunofluorescence may be used to measure the antigen binding activity of the antibody of the invention. In ELISA, the antibody of the present invention is immobilized on a plate, protein of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the protein, such as a C-terminal or N-terminal fragment may be used as a protein. BIAcore (Pharmacia) may be used to evaluate the activity of the antibody according to the present invention.

The above methods allow for the detection or measurement of the protein of the invention, by exposing the antibody of the invention to a sample assumed to contain the protein of the invention, and detecting or measuring the immune complex formed by the antibody and the protein.

Because the method of detection or measurement of the protein according to the invention can specifically detect or measure a protein, the method may be useful in a variety of experiments in which the protein is used.

The present invention also provides a polynucleotide which hybridizes with the DNA encoding human or mouse Gros1 protein (SEQ ID NOs:1, 3, 5, or 7) or the complementary strand thereof, and which comprises at least 15 nucleotides. The polynucleotide of the present invention is preferably a polynucleotide which specifically hybridizes with the DNA encoding the protein of the present invention. The term "specifically hybridize" as used herein, means that cross-hybridization does not occur significantly with DNA encoding other proteins, under the usual hybridizing conditions, preferably under stringent hybridizing conditions. Such polynucleotides include, probes, primers, nucleotides and nucleotide derivatives (for example, antisense oligonucleotides and ribozymes), which specifically hybridize with DNA encoding the protein of the invention or its complementary strand. Moreover, such polynucleotide can be utilized for the preparation of DNA chip.

The present invention includes an antisense oligonucleotide that hybridizes with any site within the nucleotide sequence any one of SEQ ID NO:1, 3, 5 or 7. This antisense oligonucleotide is preferably against at least 15 continuous nucleotides of the nucleotide sequence any one of SEQ ID NO:1, 3, 5 or 7. The above-mentioned antisense oligonucleotide, which contains an initiation codon in the above-mentioned at least 15 continuous nucleotides, is even more preferred.

Derivatives or modified products of antisense oligonucleotides can be used as antisense oligonucleotides. Examples of such modified products include lower alkyl phosphonate modifications such as methyl-phosphonate-type or ethyl-phosphonate-type, phosphorothioate modifications and phosphoroamidate modifications.

The term "antisense oligonucleotides" as used herein means, not only those in which the nucleotides corresponding to those constituting a specified region of a DNA or mRNA are entirely complementary, but also those having a mismatch of one or more nucleotides, as long as the DNA or mRNA and the antisense oligonucleotide can specifically hybridize with the nucleotide sequence of SEQ ID NO:1, 3, 5 or 7.

Such polynucleotides are contained as those having, in the "at least 15 continuous nucleotide sequence region", a homology of at least 70% or higher, preferably at 80% or higher, more preferably 90% or higher, even more preferably 95% or higher. The algorithm stated herein can be used to determine the homology. Such polynucleotides are useful as probes for the isolation or detection of DNA encoding the protein of the invention as stated in a later example or as a primer used for amplifications.

The antisense oligonucleotide derivatives of the present invention act upon cells producing the protein of the invention by binding to the DNA or mRNA encoding the protein, inhibiting its transcription or translation, promoting the degradation of the mRNA, and inhibiting the expression of the protein of the invention, thereby resulting in the inhibition of the protein's function.

An antisense oligonucleotide derivative of the present invention can be made into an external preparation, such as a liniment or a poultice, by mixing with a suitable base material which is inactive against the derivatives.

Also, as needed, the derivatives can be formulated into tablets, powders, granules, capsules, liposome capsules, injections, solutions, nose-drops and freeze-drying agents by adding excipients, isotonic agents, solubilizers, stabilizers, preservatives, pain-killers, and such. These can be prepared by following usual methods.

The antisense oligonucleotide derivative is given to the patient by directly applying onto the ailing site or by injecting into a blood vessel so that it will reach the site of ailment. An antisense-mounting medium can also be used to increase durability and membrane-permeability. Examples are, liposome, poly-L-lysine, lipid, cholesterol, lipofectin or derivatives of these.

The dosage of the antisense oligonucleotide derivative of the present invention can be adjusted suitably according to the patient's condition and used in desired amounts. For example, a dose range of 0.1 to 100 mg/kg, preferably 0.1 to 50 mg/kg can be administered.

The antisense oligonucleotide of the invention inhibits the expression of the protein of the invention and is thereby useful for suppressing the biological activity of the protein of the invention. Also, expression-inhibitors, comprising the antisense oligonucleotide of the invention, are useful in the point that they can inhibit the biological activity of the protein of the invention.

Moreover, the present invention provides a method of screening for a compound that binds to the protein of the present invention by using the protein of the present invention. This screening method comprises the steps of: (a) contacting the protein of the present invention or a partial peptide thereof with a subject sample, (b) detecting the binding activity between the protein of the present invention or the partial peptide thereof and the subject sample, and (c) selecting a compound that binds to the protein of the present invention or the partial peptide thereof.

The protein of the present invention to be used for screening may be a recombinant protein or a protein derived from the nature, or a partial peptide thereof. Any subject sample, for example, cell extracts, cell culture supernatant, products of fermenting microorganism, extracts from marine organism, plant extracts, purified or crude proteins, peptides, non-peptide compounds, synthetic micromolecular compounds and natural compounds, can be used. The protein of the present invention to be contacted with a subject sample can be, for example, a purified protein, a soluble protein, a form bound to a carrier, or a fusion protein fused with other proteins.

As a method of screening for proteins, for example, that bind to the protein of the present invention using the protein of the present invention, many methods well known by a person skilled in the art can be used. Such a screening can be conducted by, for example, immunoprecipitation method, specifically, in the following manner. The gene encoding the protein of the present invention is expressed in animal cells and so on by inserting the gene to an expression vector for foreign genes, such as pSV2neo, pcDNA I, and pCD8. The promoter to be used for the expression may be any promoter that can be used commonly and include, for example, the SV40 early promoter (Rigby in Williamson (ed.), Genetic Engineering, vol. 3. Academic Press, London, p. 83-141 (1982)), the EF-1α promoter (Kim et al., Gene, 91:217-223, 1990), the CAG promoter (Niwa et al., Gene, 108:193-200, 1991), the RSV LTR promoter (Cullen, Methods in Enzymology, 152:684-704, 1987) the SRα promoter (Takebe et al., Mol. Cell. Biol., 8:466, 1988), the CMV immediate early promoter (Seed et al., Proc. Natl. Acad. Sci. USA, 84:3365-3369, 1987), the SV40 late promoter (Gheysen et al., J. Mol. Appl. Genet., 1:385-394, 1982), the Adenovirus late promoter (Kaufman et al., Mol. Cell. Biol., 9:946, 1989), the HSV TK promoter and so on. The introduction of the gene into animal cells to express a foreign gene can be performed according to any methods, for example, the electroporation method (Chu et al., Nucl. Acids Res., 15:1311-1326, 1987), the calcium phosphate method (Chen et al., Mol. Cell. Biol., 7:2745-2752, 1987), the DEAE dextran method (Lopata et al., Nucl. Acids Res., 12:5707-5717, 1984; Sussman et al., Mol. Cell. Biol., 4:1642-1643, 1985), the Lipofectin method (Derijard, Cell, 7:1025-1037, 1994; Lamb et al., Nature Genetics, 5:22-30, 1993; Rabindran et al., Science, 259:230-234, 1993), and so on. The protein of the present invention can be expressed as a fusion protein comprising a recognition site (epitope) of a monoclonal antibody by introducing the epitope of the monoclonal antibody, whose specificity has been revealed, to the N- or C-terminus of the protein of the present invention. A commercially available epitope-antibody system can be used (Experimental Medicine, 13:85-90, 1995). Vectors which can express a fusion protein with, for example, β-galactosidase, maltose binding protein, glutathione S-transferase, green florescence protein (GFP) and so on by the use of its multiple cloning sites are commercially available.

A fusion protein prepared by introducing only small epitopes consisting of several to a dozen amino acids so as not to change the property of the protein of the present invention by the fusion is also reported. Epitopes, such as polyhistidine (His-tag), influenza aggregate HA, human c-myc, FLAG, Vesicular stomatitis virus glycoprotein (VSV-GP), T7 gene 10 protein (T7-tag), human simple herpes virus glycoprotein (HSV-tag), E-tag (an epitope on monoclonal phage), and such, and monoclonal antibodies recognizing them can be used as the epitope-antibody system for screening proteins binding to the protein of the present invention (Experimental Medicine, 13:85-90, 1995).

In immunoprecipitation, an immune complex is formed by adding these antibodies to cell lysate prepared by using an appropriate detergent. The immune complex consists of the protein of the present invention, a protein comprising the binding ability with the protein, and an antibody. Immunoprecipitation can be also conducted by using antibodies against the protein of the present invention, besides using antibodies against the above epitopes. An antibody against the protein of the present invention can be prepared, for example, by introducing a gene encoding the protein of the present invention to an appropriate E. coli expression vector, expressing the gene in E. coli, purifying the expressed protein, and immunizing rabbits, mice, rats, goats, domestic fowls and such against the protein. The antibody can be also prepared by immunizing the above animals against a synthesized partial peptide of the protein of the present invention.

An immune complex can be precipitated, for example by Protein A Sepharose or Protein G sepharose when the antibody is a mouse IgG antibody. If the protein of the present invention is prepared as a fusion protein with an epitope, such as GST, an immune complex can be formed in the same manner as in the use of the antibody against the protein of the present invention, by using a substance specifically binding to these epitopes, such as glutathione-Sepharose 4B.

Immunoprecipitation can be performed by following or according to, for example, the methods in the literature (Harlow, E. and Lane, D.: Antibodies pp. 511-552, Cold Spring Harbor Laboratory publications, New York (1988))

SDS-PAGE is commonly used for analysis of immunoprecipitated proteins and the bound protein can be analyzed by the molecular weight of the protein by using gels with an appropriate concentration. Since the protein bound to the protein of the present invention is difficult to detect by a common staining method, such as Coomassie staining or silver staining, the detection sensitivity for the protein can be improved by culturing cells in culture medium containing radioactive isotope, $^{35}$S-methionine or $^{35}$S-cystein, labeling proteins in the cells, and detecting the proteins. The target protein can be purified directly from the SDS-polyacrylamide gel and its sequence can be determined, when the molecular weight of a protein has been revealed.

As a method for isolating proteins binding to the protein of the present invention by using the protein, for example, West-Western blotting analysis (Skolnik et al., Cell, 65:83-90, 1991) can be used. Specifically, a protein binding to the protein of the present invention can be obtained by preparing a cDNA library from cells, tissues, organs (for example, tissues such as ovary, testis, and placenta or cultured cells) expected to express a protein binding to the protein of the present invention by using a phage vector (λgt11, ZAP, etc.), expressing the protein on LB-agarose, fixing the protein expressed on a filter, reacting the purified and labeled protein of the present invention with the above filter, and detecting the plaques expressing proteins bound to the protein of the present invention according to the label. The protein of the invention may be labeled by utilizing the binding between biotin and avidin, or by utilizing an antibody that specifically binds to the protein of the present invention, or a peptide or polypeptide (for example, GST) that is fused to the protein of the present invention. Methods using radioisotope or fluorescence and such may be also used.

Alternatively, in another embodiment of the screening method of the present invention, a two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton S, and Treisman R (1992) Cell 68, 597-612", "Fields S. and Sternglanz R. Trends Genet. (1994) 10:286-292").

In the two-hybrid system, the protein of the invention is fused to the SRF-binding region or GAL4-binding region and expressed in yeast cells. A cDNA library is prepared from cells expected to express a protein binding to the protein of the invention, such that the library, when expressed, is fused to the VP16 or GAL4 transcriptional activation region. The cDNA library is then introduced into the above yeast cells and the cDNA derived from the library is isolated from the positive clones detected (when a protein binding to the protein of the invention is expressed in yeast cells, the binding of the two activates a reporter gene, making positive clones detectable). A protein encoded by the cDNA can be prepared by introducing the cDNA isolated above to E. coli and expressing the protein.

As a reporter gene, for example, Ade2 gene, lacZ gene, CAT gene, luciferase gene and such can be used besides HIS3 gene.

A compound binding to the protein of the present invention can be screened using affinity chromatography. For example, the protein of the invention may be immobilized on a carrier of an affinity column, and a test sample, containing a protein capable of binding to the protein of the invention is supposed to be expressed, is applied to the column. A test sample herein may be, for example, cell extracts, cell lysates, etc. After loading the test sample, the column is washed, and proteins bound to the protein of the invention can be prepared.

The amino acid sequence of the obtained protein is analyzed, an oligo DNA is synthesized based on the sequence, and cDNA libraries are screened using the oligo DNA as a probe to obtain a DNA encoding the protein.

A biosensor using the surface plasmon resonance phenomenon may be used as a mean for detecting or quantifying the bound compound in the present invention. When such a biosensor is used, the interaction between the protein of the invention and a test compound can be observed real-time as a surface plasmon resonance signal, using only a minute amount of protein and without labeling (for example, BIAcore, Pharmacia). Therefore, it is possible to evaluate the binding between the protein of the invention and a test compound using a biosensor such as BIAcore.

The methods of screening for molecules that bind when the immobilized protein of the present invention is exposed to synthetic chemical compounds, or natural substance banks, or a random phage peptide display library, or the methods of screening using high-throughput based on combinatorial chemistry techniques (Wrighton et al., Science (US), 273: 458-64, 1996; Verdine, Nature (England), 384:11-13, 1996; Hogan, Nature (England), 384:17-19, 1996) to isolate not only proteins but chemical compounds that bind to protein of the present invention (including agonist and antagonist) are well known to one skilled in the art.

A compound isolated by the screening is a candidate for drugs which promote or inhibit the activity of the protein of the present invention, for treating or preventing diseases attributed to, for example, the functional abnormality of the protein of the present invention, or cell proliferative diseases such as cancer. A compound in which a part of the structure of the compound obtained by the present screening method having the activity of binding to the protein of the present invention is converted by addition, deletion and/or replacement, is included in the compounds obtained by the screening method of the present invention.

Moreover the present invention provides a method for screening a compound which promotes or inhibits the activity of the protein of the present invention. Since the Gros1 protein of the present invention has the activity of inhibiting cell proliferation, a compound which promotes or inhibits this activity of Gros1 protein of the present invention can be screened using this activity as an index.

This screening method includes the steps of: (a) culturing cells which express Gros1 protein in the presence of the subject sample, (b) detecting the proliferation of the cells, and (c) selecting a compound which promotes or inhibits the proliferation in comparison with the proliferation detected in the absence of the subject sample.

Any Gros1 proteins can be used for screening so long as they comprise the activity of inhibiting cell proliferation. For example, human or mouse Gros1-L protein can be used and proteins functionally equivalent to these proteins can also be used. Gros1 proteins may be expressed endogenously or exogenously by cells.

Any subject samples, for example, cell extracts, cell culture supernatant, products of fermenting microorganism, extracts of marine organism, plant extracts, purified or crude proteins, peptides, non-peptide compounds, synthetic micromolecular compounds, natural compounds, can be used. A compound obtained by the above screening for compounds that bind to the protein of the present invention can be also used as the subject compound.

The compound isolated by this screening is a candidate for agonists or antagonists of the protein of the present invention. The term "agonist" refers to molecules that activate the function of the protein of the present invention by binding thereto. Likewise, the term "antagonist" refers to molecules that inhibit the function of the protein of the present invention by binding thereto. Moreover, a compound isolated by this screening is a candidate for compounds which inhibit the in vivo interaction of the protein of the present invention with molecules (including DNAs and proteins).

Cell proliferation can be detected, for example, by determining the speed of cell proliferation, measuring the cell cycle and such, as well as by measuring the colony forming activity as described in the Examples.

The compound isolated by the screening is a candidate for drugs which promote or inhibit the activity of the protein of the present invention and can be applied to the treatment for diseases (for example, cancer, etc.) associated with the protein of the present invention.

Moreover, compound in which a part of the structure of the compound promoting or inhibiting the activity of Gros1 proteins is converted by addition, deletion and/or replacement are also included in the compounds obtainable by the screening method of the present invention.

When administrating the compound isolated by the method of the invention as a pharmaceutical for humans and other mammals, such as mice, rats, guinea-pigs, rabbits, chicken, cats, dogs, sheep, pigs, cattle, monkeys, baboons, chimpanzees, the isolated compound can be directly administered or can be formulated into a dosage form using known pharmaceutical preparation methods. For example, according to the need, the drugs can be taken orally, as sugar-coated tablets, capsules, elixirs and microcapsules, or non-orally, in the form of injections of sterile solutions or suspensions with water or any other pharmaceutically acceptable liquid. For example, the compounds can be mixed with pharmacologically acceptable carriers or medium, specifically, sterilized water, physiological saline, plant-oil, emulsifiers, suspending agents, surfactants, stabilizers, flavoring agents, excipients, vehicles, preservatives, binders and such, in a unit dose form required for generally accepted drug implementation. The amount of active ingredients in these preparations makes a suitable dosage within the indicated range acquirable.

Examples of additives that can be mixed to tablets and capsules are, binders such as gelatin, corn starch, tragacanth gum and arabic gum; excipients such as crystalline cellulose; swelling agents such as corn starch, gelatin and alginic acid; lubricants such as magnesium stearate; sweeteners such as sucrose, lactose or saccharin; flavoring agents such as peppermint, Gaultheria adenothrix oil and cherry. When the unit dosage form is a capsule, a liquid carrier, such as oil, can also be further included in the above ingredients. Sterile composites for injections can be formulated following normal drug implementations using vehicles such as distilled water used for injections.

Physiological saline, glucose, and other isotonic liquids including adjuvants, such as D-sorbitol, D-mannnose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, non-ionic surfactants, such as Polysorbate 80 (TM) and HCO-50.

Sesame oil or Soy-bean oil can be used as a oleaginous liquid and may be used in conjunction with benzyl benzoate or benzyl alcohol as a solubilizers and may be formulated with a buffer, such as phosphate buffer and sodium acetate buffer; a pain-killer, such as procaine hydrochloride; a stabilizer, such as benzyl alcohol, phenol; and an anti-oxidant. The prepared injection may be filled into a suitable ampule.

Methods well known to one skilled in the art may be used to administer the inventive pharmaceutical compound to patients, for example as intraarterial, intravenous, percutaneous injections and also as intranasal, transbronchial, intramuscular or oral administrations. The dosage and method of administration vary according to the body-weight and age of a patient and the administration method; however, one skilled in the art can routinely select them. If said compound is encodable by a DNA, the DNA can be inserted into a vector for gene therapy and the vector administered to perform the therapy. The dosage and method of administration vary according to the body-weight, age, and symptoms of a patient but one skilled in the art can select them suitably.

For example, although there are some differences according to the symptoms, the dose of a compound that binds with the protein of the present invention and regulates its activity is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kgs of body-weight.

All publications and patents cited herein are incorporated by reference in their entirety.

DETAILED DESCRIPTION

The present invention is illustrated in details by following Examples, but is not restricted to these Examples.

Example 1

Cloning and Sequence of Gros1 cDNA

It is known that the comparison of the proteins contained in the Triton X-100 insoluble factions of the plasma membrane of mouse normal cells (CMEF) and immortalized cells (NIH3T3) revealed that the protein (p33), about 30 kDa in size, present in NIH3T3 is not contained in CMEF (Wadhwa et al., Mutat. Res., 256:243-254, 1991). This protein was isolated by SDS-PAGE and anti-p33 polyclonal antibody was prepared by a standard method. A novel gene Gros1-L was obtained from an RS-4 cell cDNA library (Wadhwa et al., J.

Figure 1:
FIG. 1 shows the alignments for the mouse Gros1 sequence and the EST sequence.

Biol. Chem., 268:6615-6621, 1993) by immunoscreening using this antibody. The sequence of this gene was novel, and no homologous sequences were found in the DNA sequence data bank. Screening of the human testis library (prepared based on pCMV-SPORT (GIBCO BRL Cat. #10419-018); D'Alessio et al., Focus, 12:47, 1990; Kriegler, M., 1990, Gene Transfer and Expression: A Laboratory Manual, Stockton Press, New York, N.Y.; Sambrook, J. et al., 1989, Molecular Cloning: A Laboratory Manual, 2$^{nd}$ Edition. Cold Spring Harbor Laboratory, Cold Spring Harbor, N.Y.; Li et al., Bio-Techniques, 16:722, 1994) using a $^{32}$P labeled mouse Gros1 probe identified two types of clones (human Gros1-L and Gros1-S). Mouse Gros1-S was identified by searching the EST data using the nucleotide sequences of the obtained mouse Gros1 cDNA fragments and connecting overlapped clones (FIG. 1). This EST contained a 94 by deletion in comparison with mouse Gros1-L or other ESTs, and was predicted to generate a protein (mouse Gros1-S) shorter than the non-deleted type (mouse Gros1-L).

Figure 2:
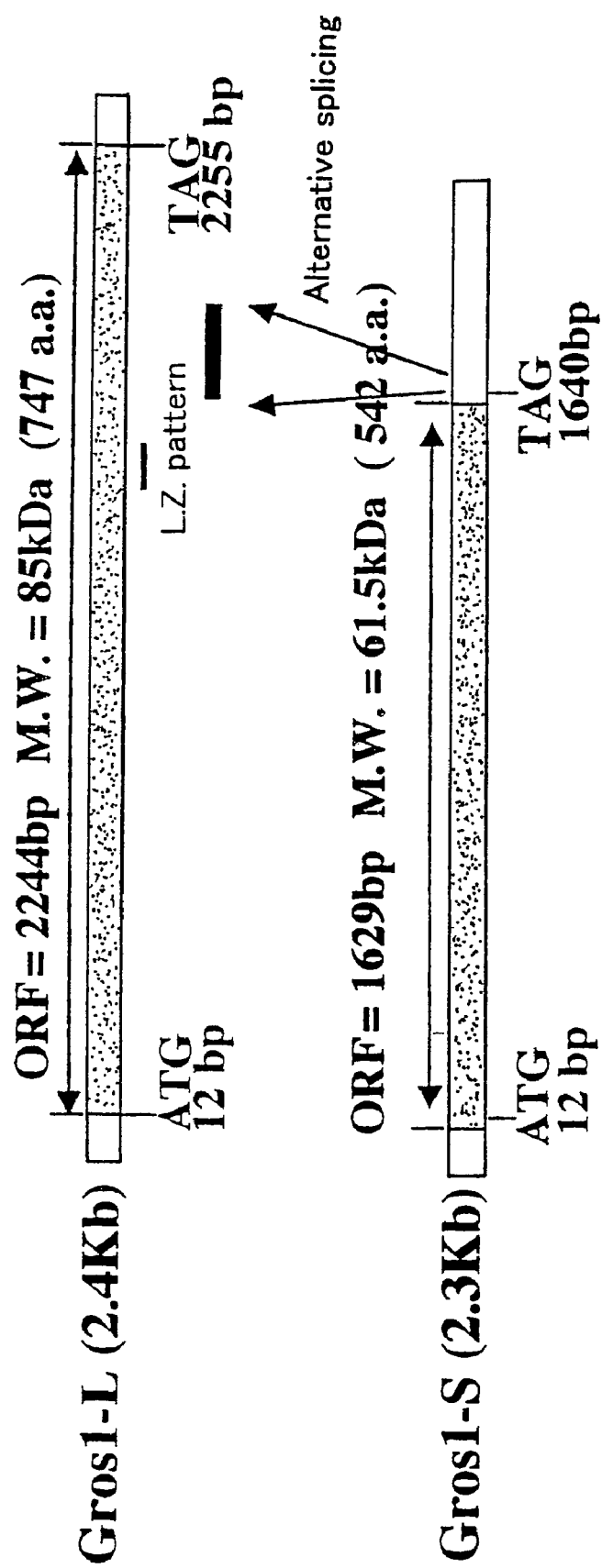
FIG. 2 shows the splicing form for cDNA of mouse Gros1.
Figure 3:
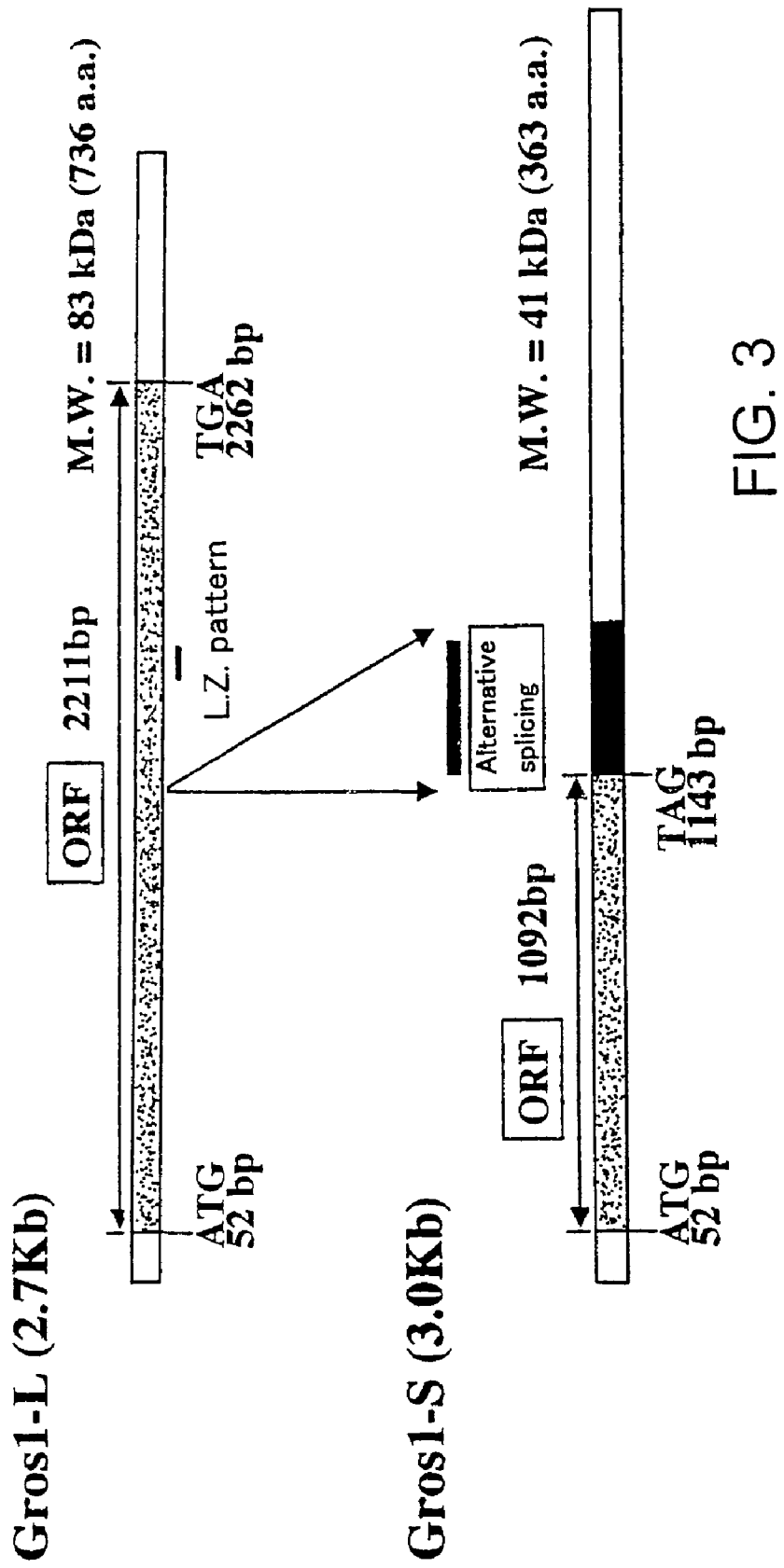
FIG. 3 shows the splicing form for cDNA of human Gros1.

SEQ ID NOs:5 and 7 show the full length nucleotide sequences of mouse Gros1-L cDNA and the full length nucleotide sequence of mouse Gros1-S cDNA obtained by the cloning using EST search, respectively. Amino acid sequences deduced from these nucleotide sequences are shown in SEQ ID NOs:6 and 8, respectively. It was revealed that each of the obtained full-length cDNA sequences shared 85.9% homology with the novel basement membrane-associated proteoglycan (leprecan) isolated from rat cDNA in the DNA sequence data bank. The cDNA obtained by immunoscreening (mouse Gros1-L) and the cDNA obtained by the cloning using EST search encoded a mouse Gros1-S, an 85 kDa protein consisting of 747 amino acids and a 61.5 kDa protein consisting of 542 amino acids (FIG. 2), respectively, having 90.9% homology with the rat leprecan in the protein data bank. Moreover, the above human 3.0 Kb clone cDNA (SEQ ID NO:1) and the cDNA of 2.7 kb clone (SEQ ID NO:3) having 83.9% homology with the mouse Gros1 were revealed to have 81.9% homology with the rat leprecan in the DNA sequence data bank. The obtained 3.0 Kb clone cDNA (SEQ ID NO:1) encoded human Gros1-S of 41 kDa consisting of 363 amino acids (SEQ ID NO:2), and the 2.7 Kb clone cDNA (SEQ ID NO:3) encoded human Gros1-L of 83 kDa consisting of 736 amino acids (SEQ ID NO:4) (FIG. 3), each having 83.0% homology with the leprecan within the protein data-bank. Although no matching DNA sequences were found, analysis of amino acid sequences by motif search revealed that the amino acid sequences in mouse and human Gros1-L partially comprise the leucine zipper structure frequently found in transcriptional factors.

Example 2

Preparation of Recombinant Gros1

The cDNA at 183-1055 within the mouse Gros1-L cDNA open reading frame was amplified by the PCR reaction (94° C. for 1 min, 55° C. for 1 min, and 72° C. for 3 min, 25 cycles) using a sense primer comprising the BamHI site (SEQ ID NO:9) and an antisense primer comprising the HindIII site (SEQ ID NO:10), and the obtained product was inserted into pGEM-T easy vector (Promega) using Rapid Ligation Kit (Boehringer Mannheim). The mixture solution of E. coli JM109 competent cells (TOYOBO) and the vector were treated at 42° C. for 1 min, spread on an ampicillin plate, and cultured for 1 day, and colonies were collected for cloning. To prepare the histidine-tagged protein, the cloned pGEM-T/Gros1 vector was cleaved at BamH I-Hind III sites, ligated with pQE30 (Qiagen), and digested at the same restriction sites by the same manner as above, and colonies were collected to obtain plasmids. E. coli M15 (Qiagen) was cultured until the absorbance at 580 nm reached 0.6, at which point the cells were transformed by the collected plasmids, and proteins were produced by inducing at 37° C. for 3 hours with 0.2 mM IPTG. Lysate of this E. coli was separated by SDS-PAGE method and detection was conducted by the Western blot analysis with the histidine antibody and Gros1 antibody described below. As a result, it was confirmed that a 40 kDa protein was synthesized. The size of the recombinant protein was as predicted. No signals could be detected by the Western blot analysis using the anti-p33 polyclonal antibody in the same manner.

Example 3

Northern Blot Analysis

Figure 4:
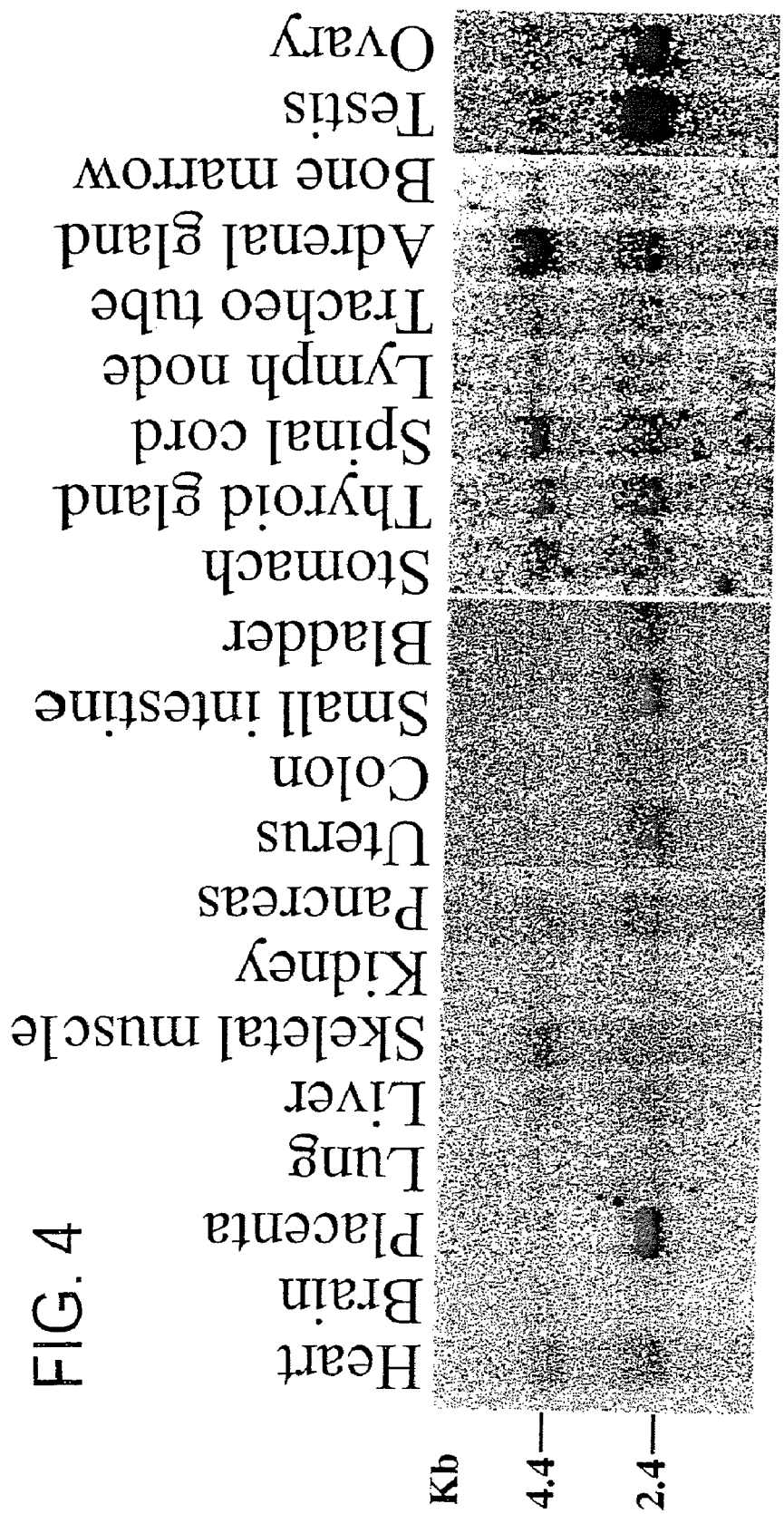
FIG. 4 shows a photograph indicating the result of Northern analysis in mouse tissues using the mouse Gros1 cDNA probe.
Figure 5:
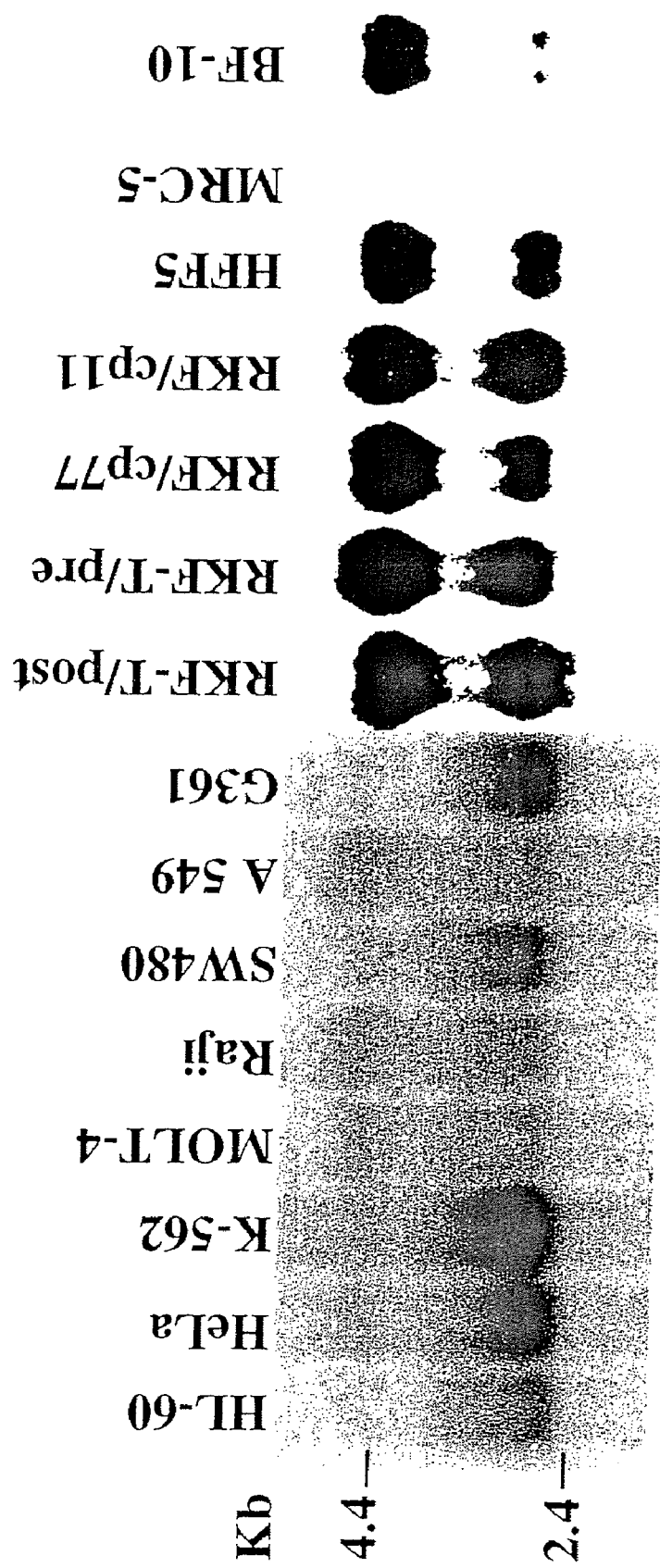
FIG. 5 shows photographs indicating the result of Northern analysis in human cells using the mouse Gros1 cDNA probe.
Figures 6A, 6B:
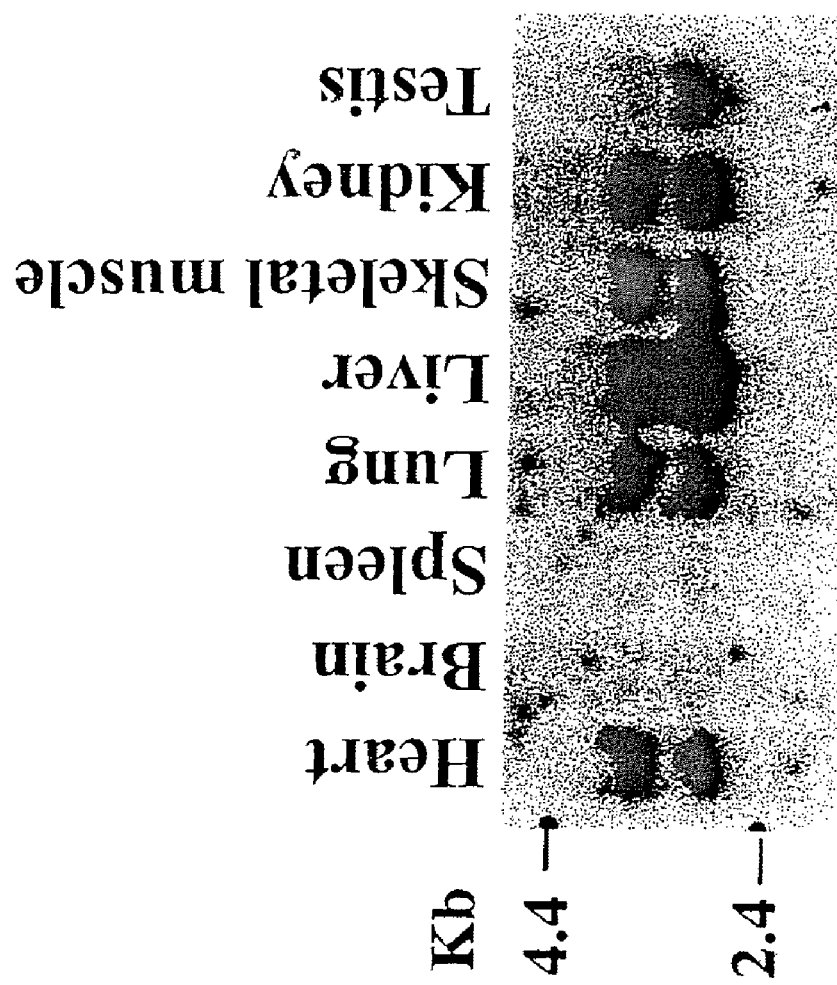
FIG. 6 shows a photograph indicating the result of Northern analysis in human tissues using the mouse Gros1 cDNA probe.

Northern blot analysis was conducted by purchasing a membrane on which 2 μg of mRNA from various mouse, human tissues per lane were loaded (Clontech laboratories, Palo alto, CA). The gene fragment of mouse Gros1-L plasmid was used as a probe. Condition for the hybridization was as follows: "Rapid-hyb buffer" (Amersham LIFE SCIENCE) was used, and after prehybridization at 68° C. for 30 min, the labeled probes were added, and the solution was incubated at 68° C. for 2 hours to perform hybridization. Then washing was conducted 3 times in 2×SSC, 0.01% SDS at room temperature for 20 min, then 3 times in 1×SSC, 0.1% SDS at 37° C. for 20 min, and twice in 1×SSC, 0.1% SDS at 50° C. for 20 min. Detection was performed by autoradiography. Northern blot analysis showed that the 4.4 kb and 2.5 kb bands were weakly expressed in most tissues in human, except for testis, ovary, and placenta. In contrast, in testis, ovary, and placenta, very strong expression was observed (FIG. 4). Higher expression of mRNA in human cultured cells was observed than in tissues. Moreover, in human normal cultured cells, the expression amount of the 2.5 kb mRNA was nearly 10 times as high as that for the mRNA of 4.4 kb (FIG. 5). In mouse, the 3.5 kb and 2.5 kb bands were weakly expressed in most tissues, except for brain, spleen and testis. No expression was observed in brain or spleen, and in testis only the 2.5 kb band was expressed. In testis and ovary, only the short type of Gros1 mRNAs was detected. It was shown that the expression dramatically disappeared at the 11$^{th}$ day during developmental process (FIG. 6).

Example 4

Location on the Chromosomes

The locations of the genes of the present invention were determined by using a sense primer (SEQ ID NO:11) and an antisense primer (SEQ ID NO:12) specific to human Gros1, with a radiation hybrid panel. As a result, they were found to be present on chromosome 1p31 in human. In mouse, they were deduced to be present on chromosome 4.

Example 5

Preparation of Antibodies Specifically Binding to the Gros1 Proteins

Antibodies against the recombinant protein deduced from the gene sequence of Gros1 were prepared. Specifically, the recombinant mouse Gros1-L protein with the histidine-tag prepared in Example 2 was purified by a nickel column; rabbits were immunized to extract the serum 4 times stepwise; and, finally, exsanguinations were conducted. Polyclonal antibodies were prepared by purifying this serum using the protein A column. It was confirmed that this anti-Gros1 polyclonal antibody recognizes Gros1 protein by separating the recombinant histidine-tagged human Gros1-L protein on the gel by SDS-PAGE, and detecting by the Western blot analysis.

Example 6

Western Blot Analysis

Western blot analysis on the lysate of human normal lung fibroblast cell, MRC-5, with the above Gros1 polyclonal antibodies detected a band about 83 kDa and another about 41 kDa which were expected from the cDNA sequence. The fact that two bands were detected is consistent with the fact that two types of transcripts, one of about 4.4 and the other of about 2.5 kb, respectively, were detected in the Northern analysis. Interestingly, in HeLa cells, in which only the long band was detected by Northern analysis, only the 83 kDa band was detected by the Western analysis. On the other hand, in NIH3T3 cells, not only the band of about 85 kDa was detected by anti-Gros1 antibody, but also bands with the size of 61.5, 41, 34 and 32 kDa were detected. The bands of about 85 kDa and 61.5 kDa correspond to mouse Gros1-L and mouse Gros1-S, respectively, and the other bands correspond presumably to proteins cleaved or modified endogenously. In COS7 cells, 60, 40 and 34 kDa bands were detected. The cDNAs encoding either human Gros1-L or S were inserted into expression vectors and transfected into COS7 cells. As the expression vector, pCMV-SPORT Vector (GIBCO BRL) used in the screening of human testis library was used. As a result of Western blot analysis using anti-Gros1 antibody, either an 83 kDa band or 41 kDa band corresponding to the cDNA sequence was detected. In COS7 cells, in which this plasmid encoding GFP-Gros1 fusion protein described below was transfected, production of proteins corresponding to the sizes of Gros1-L or Gros1-S (115 kDa and 72 kDa, respectively) was confirmed by Western blot analysis after SDS-PAGE.

Example 7

Localization of the Genes in the Cell

Figure 7:
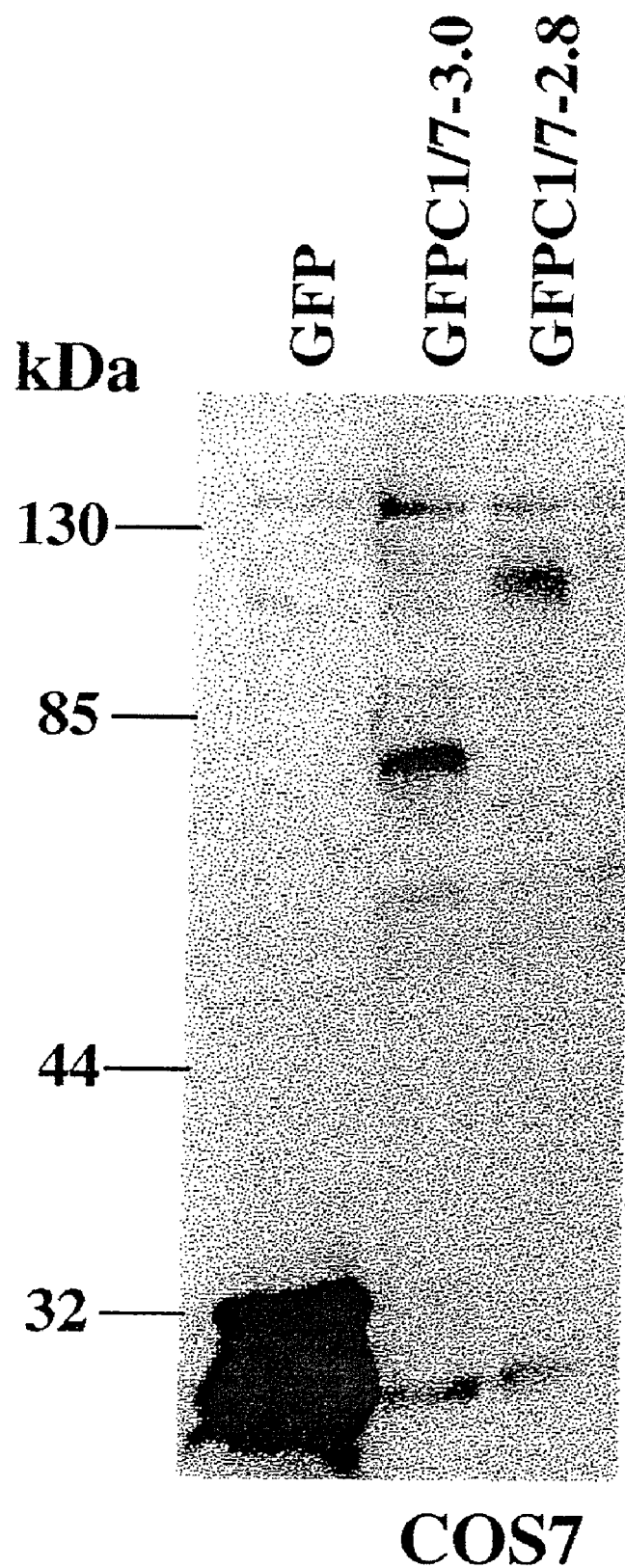
FIG. 7 shows a photograph indicating the result of Western analysis for human GFP-Gros1L and GFP-Gros1S expressed in COST.
Figure 8:
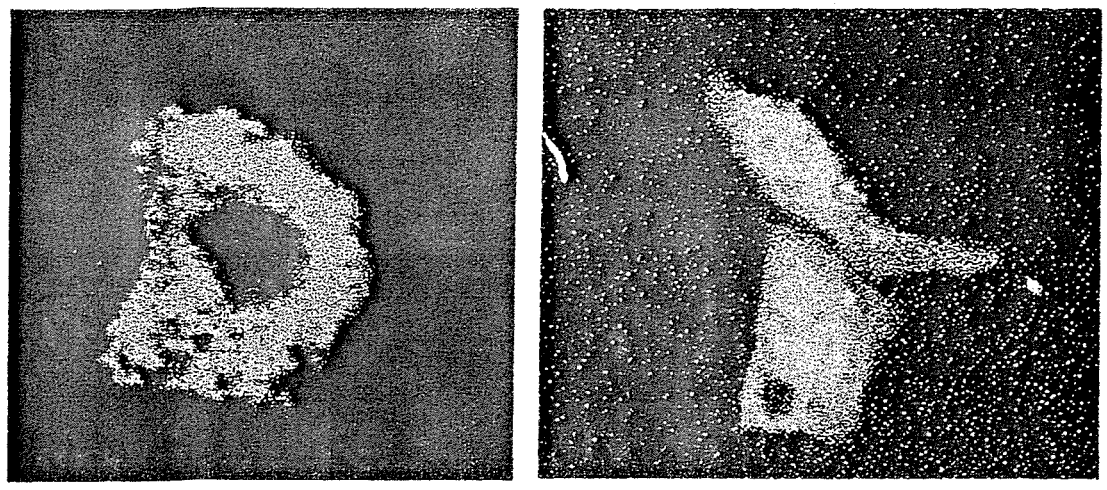
FIG. 8 shows photographs indicating localization of human GFP-Gros1L and human GFP-Gros1S in cells.

Two types of human Gros1 cDNA were amplified by PCR using sense (SEQ ID NO:13) and antisense (SEQ ID NO:14, 15) primers designed so as to comprise two types of open reading frames corresponding to human Gros1-L and S. "GFPC1/7-3.0", which expresses the fusion protein of human Gros1-S, and "GFPC1/7-2.7", which expresses the fusion protein of human Gros1-L, were prepared by inserting these genes to the C terminal region of GFP ORF in pEGFP-C1 (Clontech). With the usage of Tfx-50 (Promega), these plasmids encoding the GFP-Gros1 fusion protein and the controls plasmids encoding only the GFP were transfected into COS7 cells growing on the cover glass. The cells were fixed with 4% formaldehyde, 24 hours after the transfection, and were washed three times with PBS. The cells were observed with an epifluorescence Olympus BH-2 microscope. As a result, the two types of proteins fused with different types of Gros1 full-length sequences were both localized in the cytoplasm (FIGS. 7 and 8).

Example 8

Proliferation Repressing Activity

The Gros1 mutant cDNA/pBluescript encoding only the 369 amino acids at the N-terminus of mouse Gros1-L isolated by screening was cleaved with EcoRI, and ligated in the same manner as in Example 2, with SRa expression vector (Mol. Cell. Biol., 8:466-472, 1988), and treated with the restriction enzyme EcoRI. As a result, two clones, in sense and antisense directions, respectively, were obtained. To isolate a gene encoding the full-length mouse Gros1, EST clone AA49892A, which showed homology with mouse Gros1, was purchased from Genome System. The EST clone and Gros1 cDNA/pBluescript were both treated with restriction enzymes ScaI and NotI, and the gene fragments were ligated in the same manner as in Example 2 to obtain the mouse Gros1-L gene. This Gros1-L gene fragment was further treated with restriction enzymes at the EcoRI-NotI site and ligated to the SRα expression vector treated with restriction enzymes at the same site in the same manner as in Example 2. As a result, the SRa/Gros 1-L sense clone which expresses mouse Gros1-L was isolated.

Figure 9:
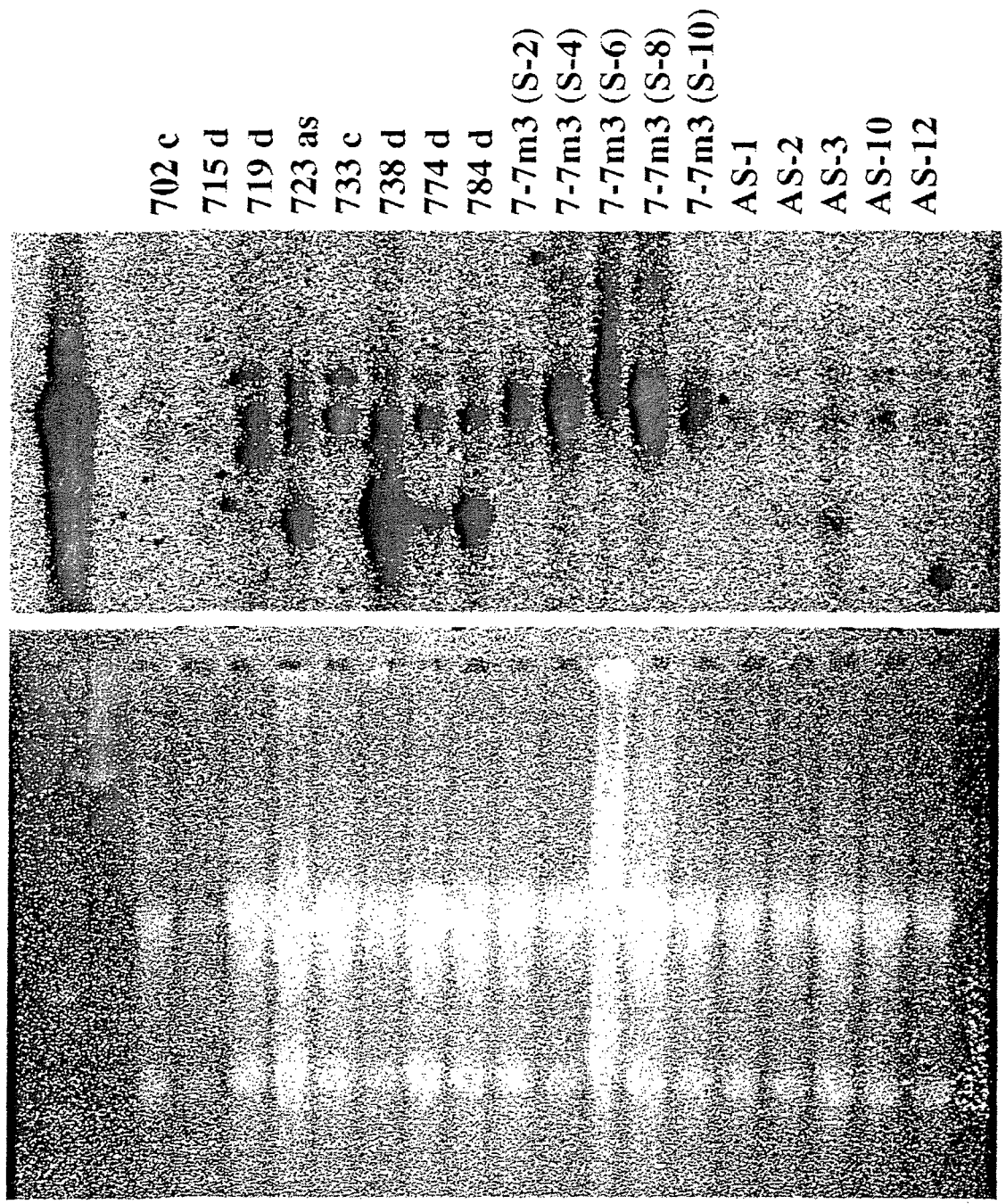
FIG. 9 shows photographs depicting the result of Northern analysis in NIH3T3 cells to which mouse Gros1L, Gros1 mutant and Gros1 antisense were introduced.

Six G418 resistance clones were obtained by introducing the above vectors into NIH3T3 cells and expression of Gros1 in each vector was confirmed by Northern blot analysis (FIG. 9). Among these, a clone in sense direction with especially high expression and a clone in antisense direction in which endogenous Gros1 transcript was rarely detected by Northern analysis were subjected to the colony forming activity test.

500 cells of each clone were spread on a 10 cm dish, and cultured for 2 weeks by replacing the medium once every three days. The cells were fixed with PBS containing 4% formaldehyde and stained with methylene blue to count the number of colonies. The experiments were done in triplicate.

Figure 10:
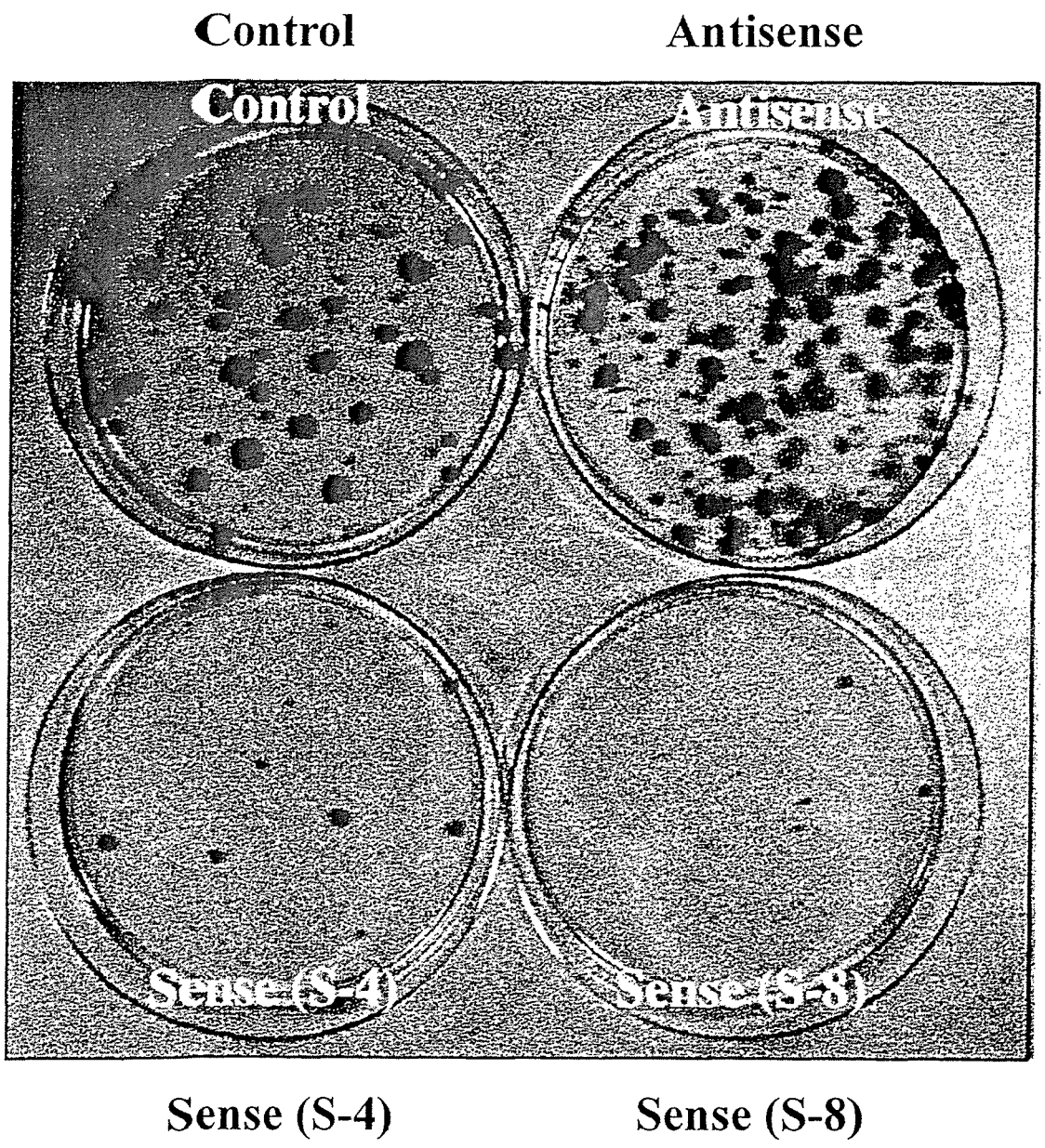
FIG. 10 shows the result of analysis of colony forming activity of NIH3T3 cells to which mouse Gros1L, Gros1 mutant and Gros1 antisense were introduced.

As a result, whereas colony formation was extremely delayed in clones transfected with Gros1-L in the sense direction, the colony formation in clones transfected with Gros1-L in the antisense direction was as about 5 times higher than the control (FIG. 10, Table 1). In Gros1-mutant in the sense direction, no decrease of colony formation was observed ("defective colonies" in Table 1). From results above, Gros1 protein was shown to have an activity to repress proliferation.

TABLE 1

| Cloned Cell | Number of colonies | |
|---|---|---|
| | Dish 1 | Dish 2 |
| Control colonies | | |
| Control 702 | 197 | 150 |
| Control 733 | 223 | 106 |
| Sense colonies | | |
| NIH3T3/7-7m3 S2 | 38 | 42 |
| NIH3T3/7-7m3 S4 | 23 | 40 |
| NIH3T3/7-7m3 S5 | 40 | 60 |
| NIH3T3/7-7m3 S6 | 33 | 9 |
| NIH3T3/7-7m3 S10 | 39 | 16 |
| Antisense colonies | | |
| #723 | 181 | 186 |
| #AS1 | 190 | 169 |
| #AS2 | 276 | 336 |
| #AS3 | 398 | 341 |
| #AS10 | 209 | 187 |
| #AS12 | 233 | 254 |
| Defective colonies | | |
| #715 | 201 | 215 |
| #719 | 179 | 193 |
| #774 | 156 | 113 |
| #784 | 103 | 117 |
| #738 | 97 | 80 |

INDUSTRIAL APPLICABILITY

The presence of non-random mutations on human chromosome 1p in many malignant tumors was proposed by cytogenetic and molecular biological approaches. These facts suggest that one or more gene mutations on chromosome 1p are important for malignant tumors. As the human Gros1 gene of the present invention is present on the chromosome 1p region and has the activity to suppress tumors, this gene may be a causative gene for these diseases. Therefore, the proteins or genes of the present invention, as well as a compound which promotes the activity of the proteins of the present invention can be used as useful tools for purifying and cloning novel factors involved in cell proliferation, and furthermore, can be used for developing pharmaceuticals for treating or preventing various tumors.

What is claimed is:

1. An isolated antibody that binds to a polypeptide consisting of the amino acid sequence of SEQ ID NO:4.

2. The antibody of claim 1, wherein the antibody is polyclonal.

3. The antibody of claim 1, wherein the antibody is monoclonal.

4. The antibody of claim 1, wherein the antibody is humanized.

5. The antibody of claim 1, wherein the antibody is human.

6. The antibody of claim 1, wherein the antibody is chimeric.

7. The antibody of claim 1, wherein the antibody is a Fab fragment, a F(ab)$_2$ fragment, an Fv fragment, or a single chain Fv (scFv).

8. The antibody of claim 1, wherein the antibody is a modified antibody.

9. A method of detecting a Gros1 polypeptide, the method comprising:
exposing the antibody of claim 1 to a sample; and
detecting an immune complex formed by the antibody and a Gros1 polypeptide in the sample.

10. A hybridoma that produces the antibody of claim 3.

11. A column to which the antibody of claim 1 is fixed.

12. The antibody of claim 9, wherein the modified antibody is conjugated with polyethylene glycol.

13. A method of purifying Gros1 polypeptide from a biological sample containing Gros1 polypeptide, the method comprising:
providing an affinity column to which the antibody of claim 1 is fixed;
contacting the biological sample with the affinity column; and
eluting Gros1 polypeptide from the affinity column.

14. A method of making the antibody of claim 1, the method comprising immunizing a non-human animal with a polypeptide consisting of the amino acid sequence of SEQ ID NO:4 or a partial peptide thereof.

15. A method of making a monoclonal antibody, the method comprising providing a hybridoma that produces the antibody of claim 3, and culturing the cell under conditions that permit production of the monoclonal antibody.

* * * * *

SEQUENCE LISTING

```
<160> NUMBER OF SEQ ID NOS: 15

<210> SEQ ID NO 1
<211> LENGTH: 2829
<212> TYPE: DNA
<213> ORGANISM: Homo sapiens
<220> FEATURE:
<221> NAME/KEY: CDS
<222> LOCATION: (52)...(1140)

<400> SEQUENCE: 1
ctccggcctt ggtggcgggt ggctggcggt tccgttaggt ctgagggagc g atg gcg      57
                                                          Met Ala
                                                           1 gta cgc gcg ttg aag ctg ctg acc aca ctg ctg gct gtc gtg gcc gct     105
Val Arg Ala Leu Lys Leu Leu Thr Thr Leu Leu Ala Val Val Ala Ala
          5                  10                  15 gcc tcc caa gcc gag gtc gag tcc gag gca gga tgg ggc atg gtg acg     153
Ala Ser Gln Ala Glu Val Glu Ser Glu Ala Gly Trp Gly Met Val Thr
     20                  25                  30 cct gat ctg ctc ttc gcc gag ggg acc gca gcc tac gcg cgc ggg gac     201
Pro Asp Leu Leu Phe Ala Glu Gly Thr Ala Ala Tyr Ala Arg Gly Asp
 35                  40                  45                  50 tgg ccc ggg gtg gtc ctg agc atg gaa cgg gcg ctg cgc tcc cgg gca     249
Trp Pro Gly Val Val Leu Ser Met Glu Arg Ala Leu Arg Ser Arg Ala
                 55                  60                  65 gcc ctc cgc gcc ctt cgc ctg cgc tgc cgc acc cag tgt gcc gcc gac     297
Ala Leu Arg Ala Leu Arg Leu Arg Cys Arg Thr Gln Cys Ala Ala Asp
             70                  75                  80 ttc ccg tgg gag ctg gac ccc gac tgg tcc ccc agc ccg gcc cag gcc     345
Phe Pro Trp Glu Leu Asp Pro Asp Trp Ser Pro Ser Pro Ala Gln Ala
         85                  90                  95 tcg ggc gcc ggc gcc ctg cgc gac ctg agc ttc ttc ggg ggc ctt ctg     393
Ser Gly Ala Gly Ala Leu Arg Asp Leu Ser Phe Phe Gly Gly Leu Leu
    100                 105                 110 cgt cgc gct gcc tgc ctg cgc cgc tgc ctc ggg ccg ccg gcc gcc cac     441
Arg Arg Ala Ala Cys Leu Arg Arg Cys Leu Gly Pro Pro Ala Ala His
115                 120                 125                 130 tcg ctc agc gaa gag atg gag ctg gag ttc cgc aag cgg agc ccc tac     489
Ser Leu Ser Glu Glu Met Glu Leu Glu Phe Arg Lys Arg Ser Pro Tyr
                135                 140                 145 aac tac ctg cag gtc gcc tac ttc aag atc aac aag ttg gag aaa gct     537
Asn Tyr Leu Gln Val Ala Tyr Phe Lys Ile Asn Lys Leu Glu Lys Ala
            150                 155                 160 gtt gct gca gca cac acc ttc ttc gtg ggc aat cct gag cac atg gaa     585
Val Ala Ala Ala His Thr Phe Phe Val Gly Asn Pro Glu His Met Glu
        165                 170                 175 atg cag cag aac cta gac tat tac caa acc atg tct gga gtg aag gag     633
Met Gln Gln Asn Leu Asp Tyr Tyr Gln Thr Met Ser Gly Val Lys Glu
    180                 185                 190
```

```
gcc gac ttc aag gat ctt gag act caa ccc cat atg caa gaa ttt cga      681
Ala Asp Phe Lys Asp Leu Glu Thr Gln Pro His Met Gln Glu Phe Arg
195                 200                 205                 210 ctg gga gtg cga ctc tac tca gag gaa cag cca cag gaa gct gtg ccc      729
Leu Gly Val Arg Leu Tyr Ser Glu Glu Gln Pro Gln Glu Ala Val Pro
                215                 220                 225 cac cta gag gcg gcg ctg caa gaa tac ttt gtg gcc tat gag gag tgc      777
His Leu Glu Ala Ala Leu Gln Glu Tyr Phe Val Ala Tyr Glu Glu Cys
            230                 235                 240 cgt gcc ctc tgc gaa ggg ccc tat gac tac gat ggc tac aac tac ctt      825
Arg Ala Leu Cys Glu Gly Pro Tyr Asp Tyr Asp Gly Tyr Asn Tyr Leu
        245                 250                 255 gag tac aac gct gac ctc ttc cag gcc atc aca gat cat tac atc cag      873
Glu Tyr Asn Ala Asp Leu Phe Gln Ala Ile Thr Asp His Tyr Ile Gln
    260                 265                 270 gtc ctc aac tgt aag cag aac tgt gtc acg gag ctt gct tcc cac cca      921
Val Leu Asn Cys Lys Gln Asn Cys Val Thr Glu Leu Ala Ser His Pro
275                 280                 285                 290 agt cga gag aag ccc ttt gaa gac ttc ctc cca tcg cat tat aat tat      969
Ser Arg Glu Lys Pro Phe Glu Asp Phe Leu Pro Ser His Tyr Asn Tyr
                295                 300                 305 ctg cag ttt gcc tac tat aac att ggg aat tat aca caa gct ggt gaa     1017
Leu Gln Phe Ala Tyr Tyr Asn Ile Gly Asn Tyr Thr Gln Ala Gly Glu
            310                 315                 320 tgt gcc aag acc tat ctt ctc ttc ttc ccc aat gac gag gtg atg aac     1065
Cys Ala Lys Thr Tyr Leu Leu Phe Phe Pro Asn Asp Glu Val Met Asn
        325                 330                 335 caa aat ttg gcc tat tat gca gct atg ctt gga gaa gaa cac acc aga     1113
Gln Asn Leu Ala Tyr Tyr Ala Ala Met Leu Gly Glu Glu His Thr Arg
    340                 345                 350 tcc atc ggc ccc cgt gag cag ggc acc tagggaaaga tgtgaccccg           1160
Ser Ile Gly Pro Arg Glu Gln Gly Thr
355                 360 gaaagtactc agtttccctg ccctggagtg ccaaggagta ccgacagcga agcctactgg   1220
aaaaagaact gcttttcttc gcttatgatg ttttttggaat tcccttttgtg gatcgggatt 1280 catggactcc agaagaaatg attcccaaga aattgcaaga gaaacagaag tgaggacctt   1340
gaagaaactg catggttgga tcagtctgat gaagcacttg aggcttcttg agcccaggca   1400
gatgtgaact cctggcaagg ggtgggcagg tccagtttgg gaagtcgggg tggagcccag   1460
ggctggccct ggaatgcagt cctcagagcg gttgtgctca taggtcagaa cgggaaacag   1520
ccgtacgcat ctcccaggag attgggaacc ttatgaagga aatcgagacc cttgtggaag   1580
agaagaccaa ggagtcactg gatgtgagca gactgacccg ggaaggtggc cccctgctgt   1640
atgaaggcat cagtctcacc atgaactcca aactcctgaa tggttaccag cgggtggtga   1700
tggacggcgt aatctctgac cacgagtgtc aggagctgca gagactgacc aatgtggcag   1760
caacctcagg agatggctac cggggtcaga cctccccaca tactcccaat gaaaagttct   1820
atggtgtcac tgtcttcaaa gccctcaagc tggggcaaga aggcaaagtt cctctgcaga   1880
gtgcccacct gtactacaac gtgacggaga aagtgcggcg catcatggag tcctacttcc   1940
gcctggatac gcccctctac ttttcctact ctcatctggt gtgccgcact gccatcgaag   2000
aggtccaggc agagaggaag gatgatagtc atccagtcca cgtggacaac tgcatcctga   2060
atgccgagac cctcgtgtgt gtcaaagagc ccccagccta caccttccgc gactacagcg   2120 ccatcctta cctaaatggg gacttcgatg gcggaaactt ttatttcact gaactggatg   2180
ccaagaccgt gacggcagag gtgcagcctc agtgtggaag agccgtggga ttctcttcag   2240
```

-continued

```
gcactgaaaa cccacatgga gtgaaggctg tcaccagggg gcagcgctgt gccatcgccc    2300
tgtggttcac cctggaccct cgacacagcg agcgggacag ggtgcaggca gatgacctgg    2360
tgaagatgct cttcagccca gaagagatgg acctctccca ggagcagccc ctggatgccc    2420
agcagggccc ccccgaacct gcacaagagt ctctctcagg cagtgaatcg aagcccaagg    2480
atgagctatg acagcgtcca ggtcagacgg atgggtgact agaccatga agaggaactc      2540 ttcttgcact ctgagctggc cagccctcg gggctgcaga gcagtgagcc tacatctgcc     2600
actcagccga ggggaccctg ctcacagcct tctacatggt gctactgctc ttggagtgga    2660
catgaccaga caccgcaccc cctggatctg gctgagggct caggacacag gcccagccac    2720
ccccaggggc ctccacaggc cgctgcataa cagcgataca gtacttaagt gtctgtgtag    2780
acaaccaaag aataaatgat tcatggtttt ttttaaaaaa aaaaaaaaa                 2829
```

<210> SEQ ID NO 2
<211> LENGTH: 363
<212> TYPE: PRT
<213> ORGANISM: Homo sapiens

<400> SEQUENCE: 2

```
Met Ala Val Arg Ala Leu Lys Leu Leu Thr Leu Leu Ala Val Val
 1               5                  10                  15

Ala Ala Ala Ser Gln Ala Glu Val Glu Ser Glu Ala Gly Trp Gly Met
                20                  25                  30

Val Thr Pro Asp Leu Leu Phe Ala Glu Gly Thr Ala Ala Tyr Ala Arg
            35                  40                  45

Gly Asp Trp Pro Gly Val Val Leu Ser Met Glu Arg Ala Leu Arg Ser
        50                  55                  60

Arg Ala Ala Leu Arg Ala Leu Arg Leu Arg Cys Arg Thr Gln Cys Ala
65                  70                  75                  80

Ala Asp Phe Pro Trp Glu Leu Asp Pro Asp Trp Ser Pro Ser Pro Ala
                85                  90                  95

Gln Ala Ser Gly Ala Gly Ala Leu Arg Asp Leu Ser Phe Phe Gly Gly
            100                 105                 110

Leu Leu Arg Arg Ala Ala Cys Leu Arg Arg Cys Leu Gly Pro Pro Ala
        115                 120                 125

Ala His Ser Leu Ser Glu Glu Met Glu Leu Glu Phe Arg Lys Arg Ser
    130                 135                 140

Pro Tyr Asn Tyr Leu Gln Val Ala Tyr Phe Lys Ile Asn Lys Leu Glu
145                 150                 155                 160

Lys Ala Val Ala Ala Ala His Thr Phe Phe Val Gly Asn Pro Glu His
                165                 170                 175

Met Glu Met Gln Gln Asn Leu Asp Tyr Tyr Gln Thr Met Ser Gly Val
            180                 185                 190

Lys Glu Ala Asp Phe Lys Asp Leu Glu Thr Gln Pro His Met Gln Glu
        195                 200                 205

Phe Arg Leu Gly Val Arg Leu Tyr Ser Glu Glu Gln Pro Gln Glu Ala
    210                 215                 220

Val Pro His Leu Glu Ala Ala Leu Gln Glu Tyr Phe Val Ala Tyr Glu
225                 230                 235                 240

Glu Cys Arg Ala Leu Cys Glu Gly Pro Tyr Asp Tyr Asp Gly Tyr Asn
                245                 250                 255

Tyr Leu Glu Tyr Asn Ala Asp Leu Phe Gln Ala Ile Thr Asp His Tyr
            260                 265                 270
```

```
Ile Gln Val Leu Asn Cys Lys Gln Asn Cys Val Thr Glu Leu Ala Ser
        275                 280                 285

His Pro Ser Arg Glu Lys Pro Phe Glu Asp Phe Leu Pro Ser His Tyr
        290                 295                 300

Asn Tyr Leu Gln Phe Ala Tyr Tyr Asn Ile Gly Asn Tyr Thr Gln Ala
305                 310                 315                 320

Gly Glu Cys Ala Lys Thr Tyr Leu Leu Phe Phe Pro Asn Asp Glu Val
                325                 330                 335

Met Asn Gln Asn Leu Ala Tyr Tyr Ala Ala Met Leu Gly Glu Glu His
            340                 345                 350

Thr Arg Ser Ile Gly Pro Arg Glu Gln Gly Thr
        355                 360

<210> SEQ ID NO 3
<211> LENGTH: 2600
<212> TYPE: DNA
<213> ORGANISM: Homo sapiens
<220> FEATURE:
<221> NAME/KEY: CDS
<222> LOCATION: (52)...(2259)

<400> SEQUENCE: 3
ctccggcctt ggtggcgggt ggctggcggt tccgttaggt ctgagggagc g atg gcg        57
                                                          Met Ala
                                                            1 gta cgc gcg ttg aag ctg ctg acc aca ctg ctg gct gtc gtg gcc gct       105
Val Arg Ala Leu Lys Leu Leu Thr Thr Leu Leu Ala Val Val Ala Ala
         5                  10                  15 gcc tcc caa gcc gag gtc gag tcc gag gca gga tgg ggc atg gtg acg       153
Ala Ser Gln Ala Glu Val Glu Ser Glu Ala Gly Trp Gly Met Val Thr
     20                  25                  30 cct gat ctg ctc ttc gcc gag ggg acc gca gcc tac gcg cgc ggg gac       201
Pro Asp Leu Leu Phe Ala Glu Gly Thr Ala Ala Tyr Ala Arg Gly Asp
 35                  40                  45                  50 tgg ccc ggg gtg gtc ctg agc atg gaa cgg gcg ctg cgc tcc cgg gca       249
Trp Pro Gly Val Val Leu Ser Met Glu Arg Ala Leu Arg Ser Arg Ala
                 55                  60                  65 gcc ctc cgc gcc ctt cgc ctg cgc tgc cgc acc cag tgt gcc gcc gac       297
Ala Leu Arg Ala Leu Arg Leu Arg Cys Arg Thr Gln Cys Ala Ala Asp
             70                  75                  80 ttc ccg tgg gag ctg gac ccc gac tgg tcc ccc agc ccg gcc cag gcc       345
Phe Pro Trp Glu Leu Asp Pro Asp Trp Ser Pro Ser Pro Ala Gln Ala
         85                  90                  95 tcg ggc gcc ggc gcc ctg cgc gac ctg agc ttc ttc ggg ggc ctt ctg       393
Ser Gly Ala Gly Ala Leu Arg Asp Leu Ser Phe Phe Gly Gly Leu Leu
    100                 105                 110 cgt cgc gct gcc tgc ctg cgc cgc tgc ctc ggg ccg ccg gcc gcc cac       441
Arg Arg Ala Ala Cys Leu Arg Arg Cys Leu Gly Pro Pro Ala Ala His
115                 120                 125                 130 tcg ctc agc gaa gag atg gag ctg gag ttc cgc aag cgg agc ccc tac       489
Ser Leu Ser Glu Glu Met Glu Leu Glu Phe Arg Lys Arg Ser Pro Tyr
                135                 140                 145 aac tac ctg cag gtc gcc tac ttc aag atc aac aag ttg gag aaa gct       537
Asn Tyr Leu Gln Val Ala Tyr Phe Lys Ile Asn Lys Leu Glu Lys Ala
            150                 155                 160 gtt gct gca gca cac acc ttc ttc gtg ggc aat cct gag cac atg gaa       585
Val Ala Ala Ala His Thr Phe Phe Val Gly Asn Pro Glu His Met Glu
        165                 170                 175
```

```
atg cag cag aac cta gac tat tac caa acc atg tct gga gtg aag gag    633
Met Gln Gln Asn Leu Asp Tyr Tyr Gln Thr Met Ser Gly Val Lys Glu
    180                 185                 190 gcc gac ttc aag gat ctt gag act caa ccc cat atg caa gaa ttt cga    681
Ala Asp Phe Lys Asp Leu Glu Thr Gln Pro His Met Gln Glu Phe Arg
195                 200                 205                 210 ctg gga gtg cga ctc tac tca gag gaa cag cca cag gaa gct gtg ccc    729
Leu Gly Val Arg Leu Tyr Ser Glu Glu Gln Pro Gln Glu Ala Val Pro
                215                 220                 225 cac cta gag gcg gcg ctg caa gaa tac ttt gtg gcc tat gag gag tgc    777
His Leu Glu Ala Ala Leu Gln Glu Tyr Phe Val Ala Tyr Glu Glu Cys
            230                 235                 240 cgt gcc ctc tgc gaa ggg ccc tat gac tac gat ggc tac aac tac ctt    825
Arg Ala Leu Cys Glu Gly Pro Tyr Asp Tyr Asp Gly Tyr Asn Tyr Leu
        245                 250                 255 gag tac aac gct gac ctc ttc cag gcc atc aca gat cat tac atc cag    873
Glu Tyr Asn Ala Asp Leu Phe Gln Ala Ile Thr Asp His Tyr Ile Gln
    260                 265                 270 gtc ctc aac tgt aag cag aac tgt gtc acg gag ctt gct tcc cac cca    921
Val Leu Asn Cys Lys Gln Asn Cys Val Thr Glu Leu Ala Ser His Pro
275                 280                 285                 290 agt cga gag aag ccc ttt gaa gac ttc ctc cca tcg cat tat aat tat    969
Ser Arg Glu Lys Pro Phe Glu Asp Phe Leu Pro Ser His Tyr Asn Tyr
                295                 300                 305 ctg cag ttt gcc tac tat aac att ggg aat tat aca caa gct ggt gaa   1017
Leu Gln Phe Ala Tyr Tyr Asn Ile Gly Asn Tyr Thr Gln Ala Gly Glu
            310                 315                 320 tgt gcc aag acc tat ctt ctc ttc ttc ccc aat gac gag gtg atg aac   1065
Cys Ala Lys Thr Tyr Leu Leu Phe Phe Pro Asn Asp Glu Val Met Asn
        325                 330                 335 caa aat ttg gcc tat tat gca gct atg ctt gga gaa gaa cac acc aga   1113
Gln Asn Leu Ala Tyr Tyr Ala Ala Met Leu Gly Glu Glu His Thr Arg
    340                 345                 350 tcc atc ggc ccc cgt gag agt gcc aag gag tac cga cag cga agc cta   1161
Ser Ile Gly Pro Arg Glu Ser Ala Lys Glu Tyr Arg Gln Arg Ser Leu
355                 360                 365                 370 ctg gaa aaa gaa ctg ctt ttc ttc gct tat gat gtt ttt gga att ccc   1209
Leu Glu Lys Glu Leu Leu Phe Phe Ala Tyr Asp Val Phe Gly Ile Pro
                375                 380                 385 ttt gtg gat ccg gat tca tgg act cca gaa gaa gtg att ccc aag aga   1257
Phe Val Asp Pro Asp Ser Trp Thr Pro Glu Glu Val Ile Pro Lys Arg
            390                 395                 400 ttg caa gag aaa cag aag tca gaa cgg gaa aca gcc gta cgc atc tcc   1305
Leu Gln Glu Lys Gln Lys Ser Glu Arg Glu Thr Ala Val Arg Ile Ser
        405                 410                 415 cag gag att ggg aac ctt atg aag gaa atc gag acc ctt gtg gaa gag   1353
Gln Glu Ile Gly Asn Leu Met Lys Glu Ile Glu Thr Leu Val Glu Glu
    420                 425                 430 aag acc aag gag tca ctg gat gtg agc aga ctg acc cgg gaa ggt ggc   1401
Lys Thr Lys Glu Ser Leu Asp Val Ser Arg Leu Thr Arg Glu Gly Gly
435                 440                 445                 450 ccc ctg ctg tat gaa ggc atc agt ctc acc atg aac tcc aaa ctc ctg   1449
Pro Leu Leu Tyr Glu Gly Ile Ser Leu Thr Met Asn Ser Lys Leu Leu
                455                 460                 465 aat ggt tac cag cgg gtg gtg atg gac ggc gta atc tct gac cac gag   1497
Asn Gly Tyr Gln Arg Val Val Met Asp Gly Val Ile Ser Asp His Glu
            470                 475                 480 tgt cag gag ctg cag aga ctg acc aat gtg gca gca acc tca gga gat   1545
Cys Gln Glu Leu Gln Arg Leu Thr Asn Val Ala Ala Thr Ser Gly Asp
        485                 490                 495
```

```
ggc tac cgg ggt cag acc tcc cca cat act ccc aat gaa aag ttc tat    1593
Gly Tyr Arg Gly Gln Thr Ser Pro His Thr Pro Asn Glu Lys Phe Tyr
500                 505                 510 ggt gtc act gtc ttc aaa gcc ctc aag ctg ggg caa gaa ggc aaa gtt    1641
Gly Val Thr Val Phe Lys Ala Leu Lys Leu Gly Gln Glu Gly Lys Val
515                 520                 525                 530 cct ctg cag agt gcc cac ctg tac tac aac gtg acg gag aaa gtg cgg    1689
Pro Leu Gln Ser Ala His Leu Tyr Tyr Asn Val Thr Glu Lys Val Arg
            535                 540                 545 cgc atc atg gag tcc tac ttc cgc ctg gat acg ccc ctc tac ttt tcc    1737
Arg Ile Met Glu Ser Tyr Phe Arg Leu Asp Thr Pro Leu Tyr Phe Ser
        550                 555                 560 tac tct cat ctg gtg tgc cgc act gcc atc gaa gag gtc cag gca gag    1785
Tyr Ser His Leu Val Cys Arg Thr Ala Ile Glu Glu Val Gln Ala Glu
    565                 570                 575 agg aag gat gat agt cat cca gtc cac gtg gac aac tgc atc ctg aat    1833
Arg Lys Asp Asp Ser His Pro Val His Val Asp Asn Cys Ile Leu Asn
580                 585                 590 gcc gag acc ctc gtg tgt gtc aaa gag ccc cca gcc tac acc ttc cgc    1881
Ala Glu Thr Leu Val Cys Val Lys Glu Pro Pro Ala Tyr Thr Phe Arg
595                 600                 605                 610 gac tac agc gcc atc ctt tac cta aat ggg gac ttc gat ggc gga aac    1929
Asp Tyr Ser Ala Ile Leu Tyr Leu Asn Gly Asp Phe Asp Gly Gly Asn
            615                 620                 625 ttt tat ttc act gaa ctg gat gcc aag acc gtg acg gca gag gtg cag    1977
Phe Tyr Phe Thr Glu Leu Asp Ala Lys Thr Val Thr Ala Glu Val Gln
        630                 635                 640 cct cag tgt gga aga gcc gtg gga ttc tct tca ggc act gaa aac cca    2025
Pro Gln Cys Gly Arg Ala Val Gly Phe Ser Ser Gly Thr Glu Asn Pro
    645                 650                 655 cat gga gtg aag gct gtc acc agg ggg cag cgc tgt gcc atc gcc ctg    2073
His Gly Val Lys Ala Val Thr Arg Gly Gln Arg Cys Ala Ile Ala Leu
660                 665                 670 tgg ttc acc ctg gac cct cga cac agc gag cgg gac agg gtg cag gca    2121
Trp Phe Thr Leu Asp Pro Arg His Ser Glu Arg Asp Arg Val Gln Ala
675                 680                 685                 690 gat gac ctg gtg aag atg ctc ttc agc cca gaa gag atg gac ctc tcc    2169
Asp Asp Leu Val Lys Met Leu Phe Ser Pro Glu Glu Met Asp Leu Ser
            695                 700                 705 cag gag cag ccc ctg gat gcc cag cag ggc ccc ccc gaa cct gca caa    2217
Gln Glu Gln Pro Leu Asp Ala Gln Gln Gly Pro Pro Glu Pro Ala Gln
        710                 715                 720 gag tct ctc tca ggc agt gaa tcg aag ccc aag gat gag cta             2259
Glu Ser Leu Ser Gly Ser Glu Ser Lys Pro Lys Asp Glu Leu
    725                 730                 735 tgacagcgtc caggtcagac ggatgggtga ctagacccat gaagaggaac tcttcttgca    2319
ctctgagctg gccagcccct cggggctgca gagcagtgag cctacatctg ccactcagcc    2379
gaggggaccc tgctcacagc cttctacatg gtgctactgc tcttggagtg gacatgacca    2439
gacaccgcac ccctggatc tggctgaggg ctcaggacac aggcccagcc acccccaggg    2499
gcctccacag gccgctgcat aacagcgata cagtacttaa gtgtctgtgt agacaaccaa    2559
agaataaatg attcatggtt tttttaaaa aaaaaaaaa a                         2600
```

<210> SEQ ID NO 4
<211> LENGTH: 736
<212> TYPE: PRT
<213> ORGANISM: Homo sapiens

```
<400> SEQUENCE: 4

Met Ala Val Arg Ala Leu Lys Leu Leu Thr Thr Leu Leu Ala Val Val
1               5                   10                  15

Ala Ala Ala Ser Gln Ala Glu Val Glu Ser Glu Ala Gly Trp Gly Met
            20                  25                  30

Val Thr Pro Asp Leu Leu Phe Ala Glu Gly Thr Ala Ala Tyr Ala Arg
        35                  40                  45

Gly Asp Trp Pro Gly Val Val Leu Ser Met Glu Arg Ala Leu Arg Ser
    50                  55                  60

Arg Ala Ala Leu Arg Ala Leu Arg Leu Arg Cys Arg Thr Gln Cys Ala
65                  70                  75                  80

Ala Asp Phe Pro Trp Glu Leu Asp Pro Asp Trp Ser Pro Ser Pro Ala
                85                  90                  95

Gln Ala Ser Gly Ala Gly Ala Leu Arg Asp Leu Ser Phe Phe Gly Gly
            100                 105                 110

Leu Leu Arg Arg Ala Ala Cys Leu Arg Arg Cys Leu Gly Pro Pro Ala
            115                 120                 125

Ala His Ser Leu Ser Glu Glu Met Glu Leu Glu Phe Arg Lys Arg Ser
130                 135                 140

Pro Tyr Asn Tyr Leu Gln Val Ala Tyr Phe Lys Ile Asn Lys Leu Glu
145                 150                 155                 160

Lys Ala Val Ala Ala His Thr Phe Val Gly Asn Pro Glu His
            165                 170                 175

Met Glu Met Gln Gln Asn Leu Asp Tyr Tyr Gln Thr Met Ser Gly Val
            180                 185                 190

Lys Glu Ala Asp Phe Lys Asp Leu Glu Thr Gln Pro His Met Gln Glu
            195                 200                 205

Phe Arg Leu Gly Val Arg Leu Tyr Ser Glu Glu Gln Pro Gln Glu Ala
210                 215                 220

Val Pro His Leu Glu Ala Ala Leu Gln Glu Tyr Phe Val Ala Tyr Glu
225                 230                 235                 240

Glu Cys Arg Ala Leu Cys Glu Gly Pro Tyr Asp Tyr Asp Gly Tyr Asn
            245                 250                 255

Tyr Leu Glu Tyr Asn Ala Asp Leu Phe Gln Ala Ile Thr Asp His Tyr
            260                 265                 270

Ile Gln Val Leu Asn Cys Lys Gln Asn Cys Val Thr Glu Leu Ala Ser
            275                 280                 285

His Pro Ser Arg Glu Lys Pro Phe Glu Asp Phe Leu Pro Ser His Tyr
            290                 295                 300

Asn Tyr Leu Gln Phe Ala Tyr Tyr Asn Ile Gly Asn Tyr Thr Gln Ala
305                 310                 315                 320

Gly Glu Cys Ala Lys Thr Tyr Leu Leu Phe Phe Pro Asn Asp Glu Val
            325                 330                 335

Met Asn Gln Asn Leu Ala Tyr Tyr Ala Ala Met Leu Gly Glu Glu His
            340                 345                 350

Thr Arg Ser Ile Gly Pro Arg Glu Ser Ala Lys Glu Tyr Arg Gln Arg
            355                 360                 365

Ser Leu Leu Glu Lys Glu Leu Leu Phe Phe Ala Tyr Asp Val Phe Gly
            370                 375                 380

Ile Pro Phe Val Asp Pro Asp Ser Trp Thr Pro Glu Glu Val Ile Pro
385                 390                 395                 400
```

```
Lys Arg Leu Gln Glu Lys Gln Lys Ser Glu Arg Thr Ala Val Arg
                405                 410                 415
Ile Ser Gln Glu Ile Gly Asn Leu Met Lys Glu Ile Glu Thr Leu Val
            420                 425                 430
Glu Glu Lys Thr Lys Glu Ser Leu Asp Val Ser Arg Leu Thr Arg Glu
        435                 440                 445
Gly Gly Pro Leu Leu Tyr Glu Gly Ile Ser Leu Thr Met Asn Ser Lys
    450                 455                 460
Leu Leu Asn Gly Tyr Gln Arg Val Val Met Asp Gly Val Ile Ser Asp
465                 470                 475                 480
His Glu Cys Gln Glu Leu Gln Arg Leu Thr Asn Val Ala Ala Thr Ser
                485                 490                 495
Gly Asp Gly Tyr Arg Gly Gln Thr Ser Pro His Thr Pro Asn Glu Lys
            500                 505                 510
Phe Tyr Gly Val Thr Val Phe Lys Ala Leu Lys Leu Gly Gln Glu Gly
        515                 520                 525
Lys Val Pro Leu Gln Ser Ala His Leu Tyr Tyr Asn Val Thr Glu Lys
    530                 535                 540
Val Arg Arg Ile Met Glu Ser Tyr Phe Arg Leu Asp Thr Pro Leu Tyr
545                 550                 555                 560
Phe Ser Tyr Ser His Leu Val Cys Arg Thr Ala Ile Glu Glu Val Gln
                565                 570                 575
Ala Glu Arg Lys Asp Asp Ser His Pro Val His Val Asp Asn Cys Ile
            580                 585                 590
Leu Asn Ala Glu Thr Leu Val Cys Val Lys Glu Pro Pro Ala Tyr Thr
        595                 600                 605
Phe Arg Asp Tyr Ser Ala Ile Leu Tyr Leu Asn Gly Asp Phe Asp Gly
    610                 615                 620
Gly Asn Phe Tyr Phe Thr Glu Leu Asp Ala Lys Thr Val Thr Ala Glu
625                 630                 635                 640
Val Gln Pro Gln Cys Gly Arg Ala Val Gly Phe Ser Ser Gly Thr Glu
                645                 650                 655
Asn Pro His Gly Val Lys Ala Val Thr Arg Gly Gln Arg Cys Ala Ile
            660                 665                 670
Ala Leu Trp Phe Thr Leu Asp Pro Arg His Ser Glu Arg Asp Arg Val
        675                 680                 685
Gln Ala Asp Asp Leu Val Lys Met Leu Phe Ser Pro Glu Glu Met Asp
    690                 695                 700
Leu Ser Gln Glu Gln Pro Leu Asp Ala Gln Gln Gly Pro Pro Glu Pro
705                 710                 715                 720
Ala Gln Glu Ser Leu Ser Gly Ser Glu Ser Lys Pro Lys Asp Glu Leu
                725                 730                 735

<210> SEQ ID NO 5
<211> LENGTH: 2416
<212> TYPE: DNA
<213> ORGANISM: Mus musculus
<220> FEATURE:
<221> NAME/KEY: CDS
<222> LOCATION: (12)...(2252)
<220> FEATURE:
<221> NAME/KEY: misc_feature
<222> LOCATION: 2376
<223> OTHER INFORMATION: n = A,T,C or G
```

<400> SEQUENCE: 5

```
ggagcaaggc c atg gcg gtg acg aaa gga ggc tgc tgg cac gat gct agc      50
            Met Ala Val Thr Lys Gly Gly Cys Trp His Asp Ala Ser
            1               5                  10 ggt cgc cgc cgc cgc ctt acg ggt tgc ggc gag tct gag ccg gga           98
Gly Arg Arg Arg Arg Leu Thr Gly Cys Gly Glu Ser Glu Pro Gly
15                  20                  25 tgg gac gtg gca gcc cct gac ctg ctt tac gca gag ggg acc gcg gcc      146
Trp Asp Val Ala Ala Pro Asp Leu Leu Tyr Ala Glu Gly Thr Ala Ala
30                  35                  40                  45 tac tcg cgc agg gac tgg ccc ggg gtg gtc ctg aac atg gag cgg gct      194
Tyr Ser Arg Arg Asp Trp Pro Gly Val Val Leu Asn Met Glu Arg Ala
                50                  55                  60 ctg cgc tcg cgg gcg gcc ctg cgt gcc ctc cgc ctg cgc tgc cgc aca      242
Leu Arg Ser Arg Ala Ala Leu Arg Ala Leu Arg Leu Arg Cys Arg Thr
            65                  70                  75 cgc tgt gcc acc gaa ctg ccg tgg gca ccg gac ctg gat ctc ggt ccg      290
Arg Cys Ala Thr Glu Leu Pro Trp Ala Pro Asp Leu Asp Leu Gly Pro
        80                  85                  90 gac ccc agc ctg agc cag gac ccg ggc gcc gcc gcc ctg cac gac ctg      338
Asp Pro Ser Leu Ser Gln Asp Pro Gly Ala Ala Ala Leu His Asp Leu
    95                  100                 105 cgc ttc ttc gga gcc gtg ctg cgc cgt gcc gcc tgc cta cgc cgc tgc      386
Arg Phe Phe Gly Ala Val Leu Arg Arg Ala Ala Cys Leu Arg Arg Cys
110                 115                 120                 125 ctc ggg ccg ccc tct gcc cac ttg ctg agt gaa gaa ctg gac ctg gag      434
Leu Gly Pro Pro Ser Ala His Leu Leu Ser Glu Glu Leu Asp Leu Glu
                130                 135                 140 ttc aac aag cgg agc ccg tac aac tac ctg cag gtc gcc tat ttc aag      482
Phe Asn Lys Arg Ser Pro Tyr Asn Tyr Leu Gln Val Ala Tyr Phe Lys
            145                 150                 155 ata aac aag ctg gag aaa gct gtg gct gcg gca cac acc ttc ttt gtg      530
Ile Asn Lys Leu Glu Lys Ala Val Ala Ala Ala His Thr Phe Phe Val
        160                 165                 170 ggc aat cct gag cac atg gag atg cgg cag aac ctc gac tat tac caa      578
Gly Asn Pro Glu His Met Glu Met Arg Gln Asn Leu Asp Tyr Tyr Gln
    175                 180                 185 acc atg tct ggg gtg aag gag gca gac ttc agg gat ctc gag gcc aag      626
Thr Met Ser Gly Val Lys Glu Ala Asp Phe Arg Asp Leu Glu Ala Lys
190                 195                 200                 205 ccc cat atg cat gag ttt cgg ctg ggg gta cga ctc tac tca gag gag      674
Pro His Met His Glu Phe Arg Leu Gly Val Arg Leu Tyr Ser Glu Glu
                210                 215                 220 aag cca cag gaa gct gtg ccc cac ctg gag gcg gca ctg caa gag tac      722
Lys Pro Gln Glu Ala Val Pro His Leu Glu Ala Ala Leu Gln Glu Tyr
            225                 230                 235 ttt gtg gcc gat gag gag tgc cgt gcc ctc tgc gaa ggg ccc tat gac      770
Phe Val Ala Asp Glu Glu Cys Arg Ala Leu Cys Glu Gly Pro Tyr Asp
        240                 245                 250 tac gac ggc tac aac tac cta gac tac agc gct gac ctc ttc cag gcc      818
Tyr Asp Gly Tyr Asn Tyr Leu Asp Tyr Ser Ala Asp Leu Phe Gln Ala
    255                 260                 265 atc aca gat cat tac gtc cag gtc ctc aac tgt aag cag aac tgt gtc      866
Ile Thr Asp His Tyr Val Gln Val Leu Asn Cys Lys Gln Asn Cys Val
270                 275                 280                 285 acg gag ctg gct tcc cac cca agt agg gaa aag ccc ttt gaa gac ttc      914
Thr Glu Leu Ala Ser His Pro Ser Arg Glu Lys Pro Phe Glu Asp Phe
                290                 295                 300
```

```
ctc cct tca cac tat aat tac cta cag ttt gcc tac tac aac att ggg      962
Leu Pro Ser His Tyr Asn Tyr Leu Gln Phe Ala Tyr Tyr Asn Ile Gly
            305                 310                 315 aac tat aca caa gct att gaa tgt gcc aag acc tac ctc ctc ttc ttt     1010
Asn Tyr Thr Gln Ala Ile Glu Cys Ala Lys Thr Tyr Leu Leu Phe Phe
    320                 325                 330 ccc aat gat gag gtg atg cac cag aat ctg gct tat tac aca gcc atg     1058
Pro Asn Asp Glu Val Met His Gln Asn Leu Ala Tyr Tyr Thr Ala Met
335                 340                 345 ctt gga gaa gaa gag gcc agc tcc atc agc ccc agg gag aat gcc gag     1106
Leu Gly Glu Glu Glu Ala Ser Ser Ile Ser Pro Arg Glu Asn Ala Glu
350                 355                 360                 365 gaa tac cga cgt cca aac ctg ttg gag aaa gaa ctg ctt ttc ttc gct     1154
Glu Tyr Arg Arg Pro Asn Leu Leu Glu Lys Glu Leu Leu Phe Phe Ala
        370                 375                 380 tat gac att ttt gga att ccc ttt gtg gat ccc gat tca tgg act cca     1202
Tyr Asp Ile Phe Gly Ile Pro Phe Val Asp Pro Asp Ser Trp Thr Pro
                385                 390                 395 gaa gaa gtg att ccc aag aga ttg caa gag aaa cag aag tct gaa cgg     1250
Glu Glu Val Ile Pro Lys Arg Leu Gln Glu Lys Gln Lys Ser Glu Arg
                    400                 405                 410 gaa aca gcc gta cgc atc tcc cag gag att ggg aac ctt atg aag gaa     1298
Glu Thr Ala Val Arg Ile Ser Gln Glu Ile Gly Asn Leu Met Lys Glu
    415                 420                 425 atc gag acc ctt gtg gaa gag aag acc aag gag tct ctg gat gtg agc     1346
Ile Glu Thr Leu Val Glu Glu Lys Thr Lys Glu Ser Leu Asp Val Ser
430                 435                 440                 445 aga ctg acc cgg gaa ggt ggt ccc ctg ctg tat gaa ggc atc agt ctc     1394
Arg Leu Thr Arg Glu Gly Gly Pro Leu Leu Tyr Glu Gly Ile Ser Leu
                    450                 455                 460 acc atg aac tcc aaa gtc ttg aat ggc tcc cag cgg gtg gtg atg gat     1442
Thr Met Asn Ser Lys Val Leu Asn Gly Ser Gln Arg Val Val Met Asp
                465                 470                 475 ggt gtg atc tct gat gat gag tgc cag gag ctg cag aga ctg acc aat     1490
Gly Val Ile Ser Asp Asp Glu Cys Gln Glu Leu Gln Arg Leu Thr Asn
            480                 485                 490 gcg gca gca act tcg gga gat ggc tac cga ggt cag acc tcc cca cac     1538
Ala Ala Ala Thr Ser Gly Asp Gly Tyr Arg Gly Gln Thr Ser Pro His
    495                 500                 505 acc cca aat gaa aag ttc tat ggt gtt act gtc ctc aaa gct ctc aag     1586
Thr Pro Asn Glu Lys Phe Tyr Gly Val Thr Val Leu Lys Ala Leu Lys
510                 515                 520                 525 ctc ggg cag gaa gga aaa gtt cct ctg cag agt gcc cgc atg tac tac     1634
Leu Gly Gln Glu Gly Lys Val Pro Leu Gln Ser Ala Arg Met Tyr Tyr
                    530                 535                 540 aac gtg aca gag aag gtg cgg cgc gtc atg gag tcc tac ttc cgc ctg     1682
Asn Val Thr Glu Lys Val Arg Arg Val Met Glu Ser Tyr Phe Arg Leu
                545                 550                 555 gac acg ccc ctc tat ttc tct tat tcc cac ttc gtg tgc cgc act gca     1730
Asp Thr Pro Leu Tyr Phe Ser Tyr Ser His Phe Val Cys Arg Thr Ala
            560                 565                 570 ata gaa gag tca cag gct gag agg aag gac agt agc cac ccc gtc cac     1778
Ile Glu Glu Ser Gln Ala Glu Arg Lys Asp Ser Ser His Pro Val His
    575                 580                 585 gtg gat aac tgc atc ctg aat gcc gaa gcc ttc atg tgt atc aag gag     1826
Val Asp Asn Cys Ile Leu Asn Ala Glu Ala Phe Met Cys Ile Lys Glu
590                 595                 600                 605 ccc cca gca tac acg ttc cgg gaa tac agc gcc atc ctt tac ctc aat     1874
Pro Pro Ala Tyr Thr Phe Arg Glu Tyr Ser Ala Ile Leu Tyr Leu Asn
                    610                 615                 620
```

-continued

```
ggc gac ttc gat gga gga aac ttt tac ttc aca gaa cta gat gcc aag    1922
Gly Asp Phe Asp Gly Gly Asn Phe Tyr Phe Thr Glu Leu Asp Ala Lys
            625                 630                 635 act gtg acg gca gag gtg cag ccc cag tgt gga agg gct gtg gga ttc    1970
Thr Val Thr Ala Glu Val Gln Pro Gln Cys Gly Arg Ala Val Gly Phe
        640                 645                 650 tct tct ggc act gag aac cca cat gga gtg aag gct gtc acc agg ggg    2018
Ser Ser Gly Thr Glu Asn Pro His Gly Val Lys Ala Val Thr Arg Gly
    655                 660                 665 cag cgc tgc gcc atc gcc ctg tgg ttc acg ctg gat cct cgg cac agt    2066
Gln Arg Cys Ala Ile Ala Leu Trp Phe Thr Leu Asp Pro Arg His Ser
670                 675                 680                 685 gag aga gac agg gtg cag gca gat gac ctg gtg aag atg ctg ttc agc    2114
Glu Arg Asp Arg Val Gln Ala Asp Asp Leu Val Lys Met Leu Phe Ser
                690                 695                 700 cca gaa gag gtg gac ctc ccc cag gaa cag ccc ctg cct gac cag cag    2162
Pro Glu Glu Val Asp Leu Pro Gln Glu Gln Pro Leu Pro Asp Gln Gln
            705                 710                 715 ggt tcg cca gag cct gga gaa gag ttt ctg cat ggt gct act gtt ctt    2210
Gly Ser Pro Glu Pro Gly Glu Glu Phe Leu His Gly Ala Thr Val Leu
        720                 725                 730 gga gtg ggc ata gca gga cac act ctt ctc tgg gct tgg ctg            2252
Gly Val Gly Ile Ala Gly His Thr Leu Leu Trp Ala Trp Leu
    735                 740                 745 taggctcaga atgcaggccc agaaccaccc tggggcctat gtaggcagct gccgtcagca   2312
gcgtgatata tttaagtgtc tgtaaagaca accaaagaat aaatgatttg tgttttaaa   2372 aagnaaaaaa aaaaaaaaat taaaaatttg cgcggccgca agaa                   2416

<210> SEQ ID NO 6
<211> LENGTH: 747
<212> TYPE: PRT
<213> ORGANISM: Mus musculus

<400> SEQUENCE: 6

Met Ala Val Thr Lys Gly Gly Cys Trp His Asp Ala Ser Gly Arg Arg
 1               5                  10                  15

Arg Arg Arg Leu Thr Gly Cys Gly Glu Ser Glu Pro Gly Trp Asp Val
            20                  25                  30

Ala Ala Pro Asp Leu Leu Tyr Ala Glu Gly Thr Ala Ala Tyr Ser Arg
        35                  40                  45

Arg Asp Trp Pro Gly Val Val Leu Asn Met Glu Arg Ala Leu Arg Ser
    50                  55                  60

Arg Ala Ala Leu Arg Ala Leu Arg Leu Arg Cys Arg Thr Arg Cys Ala
65                  70                  75                  80

Thr Glu Leu Pro Trp Ala Pro Asp Leu Asp Leu Gly Pro Asp Pro Ser
                85                  90                  95

Leu Ser Gln Asp Pro Gly Ala Ala Ala Leu His Asp Leu Arg Phe Phe
            100                 105                 110

Gly Ala Val Leu Arg Arg Ala Cys Leu Arg Arg Cys Leu Gly Pro
        115                 120                 125

Pro Ser Ala His Leu Leu Ser Glu Glu Leu Asp Leu Glu Phe Asn Lys
    130                 135                 140

Arg Ser Pro Tyr Asn Tyr Leu Gln Val Ala Tyr Phe Lys Ile Asn Lys
145                 150                 155                 160

Leu Glu Lys Ala Val Ala Ala Ala His Thr Phe Phe Val Gly Asn Pro
                165                 170                 175
```

```
Glu His Met Glu Met Arg Gln Asn Leu Asp Tyr Tyr Gln Thr Met Ser
            180                 185                 190

Gly Val Lys Glu Ala Asp Phe Arg Asp Leu Glu Ala Lys Pro His Met
        195                 200                 205

His Glu Phe Arg Leu Gly Val Arg Leu Tyr Ser Glu Glu Lys Pro Gln
    210                 215                 220

Glu Ala Val Pro His Leu Glu Ala Ala Leu Gln Glu Tyr Phe Val Ala
225                 230                 235                 240

Asp Glu Glu Cys Arg Ala Leu Cys Glu Gly Pro Tyr Asp Tyr Asp Gly
                245                 250                 255

Tyr Asn Tyr Leu Asp Tyr Ser Ala Asp Leu Phe Gln Ala Ile Thr Asp
            260                 265                 270

His Tyr Val Gln Val Leu Asn Cys Lys Gln Asn Cys Val Thr Glu Leu
        275                 280                 285

Ala Ser His Pro Ser Arg Glu Lys Pro Phe Glu Asp Phe Leu Pro Ser
    290                 295                 300

His Tyr Asn Tyr Leu Gln Phe Ala Tyr Tyr Asn Ile Gly Asn Tyr Thr
305                 310                 315                 320

Gln Ala Ile Glu Cys Ala Lys Thr Tyr Leu Leu Phe Phe Pro Asn Asp
                325                 330                 335

Glu Val Met His Gln Asn Leu Ala Tyr Tyr Thr Ala Met Leu Gly Glu
            340                 345                 350

Glu Glu Ala Ser Ser Ile Ser Pro Arg Glu Asn Ala Glu Glu Tyr Arg
        355                 360                 365

Arg Pro Asn Leu Leu Glu Lys Glu Leu Leu Phe Phe Ala Tyr Asp Ile
    370                 375                 380

Phe Gly Ile Pro Phe Val Asp Pro Asp Ser Trp Thr Pro Glu Glu Val
385                 390                 395                 400

Ile Pro Lys Arg Leu Gln Glu Lys Gln Lys Ser Glu Arg Glu Thr Ala
                405                 410                 415

Val Arg Ile Ser Gln Glu Ile Gly Asn Leu Met Lys Glu Ile Glu Thr
            420                 425                 430

Leu Val Glu Glu Lys Thr Lys Glu Ser Leu Asp Val Ser Arg Leu Thr
        435                 440                 445

Arg Glu Gly Gly Pro Leu Leu Tyr Glu Gly Ile Ser Leu Thr Met Asn
    450                 455                 460

Ser Lys Val Leu Asn Gly Ser Gln Arg Val Val Met Asp Gly Val Ile
465                 470                 475                 480

Ser Asp Asp Glu Cys Gln Glu Leu Gln Arg Leu Thr Asn Ala Ala Ala
                485                 490                 495

Thr Ser Gly Asp Gly Tyr Arg Gly Gln Thr Ser Pro His Thr Pro Asn
            500                 505                 510

Glu Lys Phe Tyr Gly Val Thr Val Leu Lys Ala Leu Lys Leu Gly Gln
        515                 520                 525

Glu Gly Lys Val Pro Leu Gln Ser Ala Arg Met Tyr Tyr Asn Val Thr
    530                 535                 540

Glu Lys Val Arg Arg Val Met Glu Ser Tyr Phe Arg Leu Asp Thr Pro
545                 550                 555                 560

Leu Tyr Phe Ser Tyr Ser His Phe Val Cys Arg Thr Ala Ile Glu Glu
                565                 570                 575

Ser Gln Ala Glu Arg Lys Asp Ser Ser His Pro Val His Val Asp Asn
            580                 585                 590
```

```
Cys Ile Leu Asn Ala Glu Ala Phe Met Cys Ile Lys Glu Pro Pro Ala
        595                 600                 605

Tyr Thr Phe Arg Glu Tyr Ser Ala Ile Leu Tyr Leu Asn Gly Asp Phe
    610                 615                 620

Asp Gly Gly Asn Phe Tyr Phe Thr Glu Leu Asp Ala Lys Thr Val Thr
625                 630                 635                 640

Ala Glu Val Gln Pro Gln Cys Gly Arg Ala Val Gly Phe Ser Ser Gly
            645                 650                 655

Thr Glu Asn Pro His Gly Val Lys Ala Val Thr Arg Gly Gln Arg Cys
        660                 665                 670

Ala Ile Ala Leu Trp Phe Thr Leu Asp Pro Arg His Ser Glu Arg Asp
    675                 680                 685

Arg Val Gln Ala Asp Asp Leu Val Lys Met Leu Phe Ser Pro Glu Glu
690                 695                 700

Val Asp Leu Pro Gln Glu Gln Pro Leu Pro Asp Gln Gln Gly Ser Pro
705                 710                 715                 720

Glu Pro Gly Glu Glu Phe Leu His Gly Ala Thr Val Leu Gly Val Gly
            725                 730                 735

Ile Ala Gly His Thr Leu Leu Trp Ala Trp Leu
        740                 745
```

<210> SEQ ID NO 7
<211> LENGTH: 2322
<212> TYPE: DNA
<213> ORGANISM: Mus musculus
<220> FEATURE:
<221> NAME/KEY: CDS
<222> LOCATION: (12)...(1637)
<220> FEATURE:
<221> NAME/KEY: misc_feature
<222> LOCATION: 2282
<223> OTHER INFORMATION: n = A,T,C or G

<400> SEQUENCE: 7

```
ggagcaaggc c atg gcg gtg acg aaa gga ggc tgc tgg cac gat gct agc       50
            Met Ala Val Thr Lys Gly Gly Cys Trp His Asp Ala Ser
              1               5                  10 ggt cgc cgc cgc cgc cgc ctt acg ggt tgc ggc gag tct gag ccg gga       98
Gly Arg Arg Arg Arg Arg Leu Thr Gly Cys Gly Glu Ser Glu Pro Gly
 15                  20                  25 tgg gac gtg gca gcc cct gac ctg ctt tac gca gag ggg acc gcg gcc      146
Trp Asp Val Ala Ala Pro Asp Leu Leu Tyr Ala Glu Gly Thr Ala Ala
 30                  35                  40                  45 tac tcg cgc agg gac tgg ccc ggg gtg gtc ctg aac atg gag cgg gct      194
Tyr Ser Arg Arg Asp Trp Pro Gly Val Val Leu Asn Met Glu Arg Ala
                 50                  55                  60 ctg cgc tcg cgg gcg gcc ctg cgt gcc ctc cgc ctg cgc tgc cgc aca      242
Leu Arg Ser Arg Ala Ala Leu Arg Ala Leu Arg Leu Arg Cys Arg Thr
             65                  70                  75 cgc tgt gcc acc gaa ctg ccg tgg gca ccg gac ctg gat ctc ggt ccg      290
Arg Cys Ala Thr Glu Leu Pro Trp Ala Pro Asp Leu Asp Leu Gly Pro
         80                  85                  90 gac ccc agc ctg agc cag gac ccg ggc gcc gcc ctg cac gac ctg          338
Asp Pro Ser Leu Ser Gln Asp Pro Gly Ala Ala Leu His Asp Leu
     95                 100                 105 cgc ttc ttc gga gcc gtg ctg cgc cgt gcc gcc tgc cta cgc cgc tgc      386
Arg Phe Phe Gly Ala Val Leu Arg Arg Ala Ala Cys Leu Arg Arg Cys
110                 115                 120                 125
```

```
                                                         -continued ctc ggg ccg ccc tct gcc cac ttg ctg agt gaa gaa ctg gac ctg gag      434
Leu Gly Pro Pro Ser Ala His Leu Leu Ser Glu Glu Leu Asp Leu Glu
            130             135             140 ttc aac aag cgg agc ccg tac aac tac ctg cag gtc gcc tat ttc aag      482
Phe Asn Lys Arg Ser Pro Tyr Asn Tyr Leu Gln Val Ala Tyr Phe Lys
        145             150             155 ata aac aag ctg gag aaa gct gtg gct gcg gca cac acc ttc ttt gtg      530
Ile Asn Lys Leu Glu Lys Ala Val Ala Ala Ala His Thr Phe Phe Val
160             165             170 ggc aat cct gag cac atg gag atg cgg cag aac ctc gac tat tac caa      578
Gly Asn Pro Glu His Met Glu Met Arg Gln Asn Leu Asp Tyr Tyr Gln
        175             180             185 acc atg tct ggg gtg aag gag gca gac ttc agg gat ctc gag gcc aag      626
Thr Met Ser Gly Val Lys Glu Ala Asp Phe Arg Asp Leu Glu Ala Lys
190             195             200             205 ccc cat atg cat gag ttt cgg ctg ggg gta cga ctc tac tca gag gag      674
Pro His Met His Glu Phe Arg Leu Gly Val Arg Leu Tyr Ser Glu Glu
            210             215             220 aag cca cag gaa gct gtg ccc cac ctg gag gcg gca ctg caa gag tac      722
Lys Pro Gln Glu Ala Val Pro His Leu Glu Ala Ala Leu Gln Glu Tyr
        225             230             235 ttt gtg gcc gat gag gag tgc cgt gcc ctc tgc gaa ggg ccc tat gac      770
Phe Val Ala Asp Glu Glu Cys Arg Ala Leu Cys Glu Gly Pro Tyr Asp
        240             245             250 tac gac ggc tac aac tac cta gac tac agc gct gac ctc ttc cag gcc      818
Tyr Asp Gly Tyr Asn Tyr Leu Asp Tyr Ser Ala Asp Leu Phe Gln Ala
        255             260             265 atc aca gat cat tac gtc cag gtc ctc aac tgt aag cag aac tgt gtc      866
Ile Thr Asp His Tyr Val Gln Val Leu Asn Cys Lys Gln Asn Cys Val
270             275             280             285 acg gag ctg gct tcc cac cca agt agg gaa aag ccc ttt gaa gac ttc      914
Thr Glu Leu Ala Ser His Pro Ser Arg Glu Lys Pro Phe Glu Asp Phe
            290             295             300 ctc cct tca cac tat aat tac cta cag ttt gcc tac tac aac att ggg      962
Leu Pro Ser His Tyr Asn Tyr Leu Gln Phe Ala Tyr Tyr Asn Ile Gly
        305             310             315 aac tat aca caa gct att gaa tgt gcc aag acc tac ctc ctc ttc ttt     1010
Asn Tyr Thr Gln Ala Ile Glu Cys Ala Lys Thr Tyr Leu Leu Phe Phe
        320             325             330 ccc aat gat gag gtg atg cac cag aat ctg gct tat tac aca gcc atg     1058
Pro Asn Asp Glu Val Met His Gln Asn Leu Ala Tyr Tyr Thr Ala Met
335             340             345 ctt gga gaa gaa gag gcc agc tcc atc agc ccc agg gag aat gcc gag     1106
Leu Gly Glu Glu Glu Ala Ser Ser Ile Ser Pro Arg Glu Asn Ala Glu
350             355             360             365 gaa tac cga cgt cca aac ctg ttg gag aaa gaa ctg ctt ttc ttc gct     1154
Glu Tyr Arg Arg Pro Asn Leu Leu Glu Lys Glu Leu Leu Phe Phe Ala
        370             375             380 tat gac att ttt gga att ccc ttt gtg gat ccc gat tca tgg act cca     1202
Tyr Asp Ile Phe Gly Ile Pro Phe Val Asp Pro Asp Ser Trp Thr Pro
            385             390             395 gaa gaa gtg att ccc aag aga ttg caa gag aaa cag aag tct gaa cgg     1250
Glu Glu Val Ile Pro Lys Arg Leu Gln Glu Lys Gln Lys Ser Glu Arg
                400             405             410 gaa aca gcc gta cgc atc tcc cag gag att ggg aac ctt atg aag gaa     1298
Glu Thr Ala Val Arg Ile Ser Gln Glu Ile Gly Asn Leu Met Lys Glu
        415             420             425 atc gag acc ctt gtg gaa gag aag acc aag gag tct ctg gat gtg agc     1346
Ile Glu Thr Leu Val Glu Glu Lys Thr Lys Glu Ser Leu Asp Val Ser
430             435             440             445
```

```
aga ctg acc cgg gaa ggt ggt ccc ctg ctg tat gaa ggc atc agt ctc     1394
Arg Leu Thr Arg Glu Gly Gly Pro Leu Leu Tyr Glu Gly Ile Ser Leu
            450                 455                 460 acc atg aac tcc aaa gtc ttg aat ggc tcc cag cgg gtg gtg atg gat     1442
Thr Met Asn Ser Lys Val Leu Asn Gly Ser Gln Arg Val Val Met Asp
            465                 470                 475 ggt gtg atc tct gat gat gag tgc cag gag ctg cag aga ctg acc aat     1490
Gly Val Ile Ser Asp Asp Glu Cys Gln Glu Leu Gln Arg Leu Thr Asn
        480                 485                 490 gcg gca gca act tcg gga gat ggc tac cga ggt cag acc tcc cca cac     1538
Ala Ala Ala Thr Ser Gly Asp Gly Tyr Arg Gly Gln Thr Ser Pro His
    495                 500                 505 acc cca aat gaa aag ttc tat ggt gtt act gtc ctc aaa gct ctc aag     1586
Thr Pro Asn Glu Lys Phe Tyr Gly Val Thr Val Leu Lys Ala Leu Lys
510                 515                 520                 525 ctc ggg cag gaa gga aaa gtt cct ctg cag agt gcc cgc acc gca ctg     1634
Leu Gly Gln Glu Gly Lys Val Pro Leu Gln Ser Ala Arg Thr Ala Leu
                530                 535                 540 caa tagaagagtc acaggctgag aggaaggaca gtagccaccc cgtccacgtg          1687
Gln gataactgca tcctgaatgc cgaagccttc atgtgtatca aggagccccc agcatacacg   1747
ttccgggaat acagcgccat cctttacctc aatggcgact tcgatggagg aaacttttac   1807
ttcacagaac tagatgccaa gactgtgacg gcagaggtgc agccccagtg tggaagggct   1867
gtgggattct cttctggcac tgagaaccca catggagtga aggctgtcac caggggggcag  1927 cgctgcgcca tcgccctgtg ttcacgctg atcctcggc acagtgagag agacagggtg    1987
caggcagatg acctggtgaa gatgctgttc agcccagaag aggtggacct cccccaggaa   2047
cagcccctgc ctgaccagca gggttcgcca gagcctggaa agagtttct gcatggtgct    2107 actgttcttg gagtgggcat agcaggacac actcttctct gggcttggct gtaggctcag   2167
aatgcaggcc cagaaccacc ctggggccta tgtaggcagc tgccgtcagc agcgtgatat   2227
atttaagtgt ctgtaaagac aaccaaagaa taaatgattt gtgttttaa aaagnaaaaa    2287 aaaaaaaaaa ttaaaaattt gcgcggccgc aagaa                              2322
```

<210> SEQ ID NO 8
<211> LENGTH: 542
<212> TYPE: PRT
<213> ORGANISM: Mus musculus

<400> SEQUENCE: 8

```
Met Ala Val Thr Lys Gly Gly Cys Trp His Asp Ala Ser Gly Arg Arg
 1               5                  10                  15

Arg Arg Arg Leu Thr Gly Cys Gly Glu Ser Glu Pro Gly Trp Asp Val
            20                  25                  30

Ala Ala Pro Asp Leu Leu Tyr Ala Glu Gly Thr Ala Ala Tyr Ser Arg
        35                  40                  45

Arg Asp Trp Pro Gly Val Val Leu Asn Met Glu Arg Ala Leu Arg Ser
    50                  55                  60

Arg Ala Ala Leu Arg Ala Leu Arg Leu Arg Cys Arg Thr Arg Cys Ala
65                  70                  75                  80

Thr Glu Leu Pro Trp Ala Pro Asp Leu Asp Leu Gly Pro Asp Pro Ser
                85                  90                  95

Leu Ser Gln Asp Pro Gly Ala Ala Ala Leu His Asp Leu Arg Phe Phe
            100                 105                 110
```

```
Gly Ala Val Leu Arg Arg Ala Ala Cys Leu Arg Cys Leu Gly Pro
        115                 120                 125

Pro Ser Ala His Leu Leu Ser Glu Glu Leu Asp Leu Glu Phe Asn Lys
    130                 135                 140

Arg Ser Pro Tyr Asn Tyr Leu Gln Val Ala Tyr Phe Lys Ile Asn Lys
145                 150                 155                 160

Leu Glu Lys Ala Val Ala Ala Ala His Thr Phe Phe Val Gly Asn Pro
                165                 170                 175

Glu His Met Glu Met Arg Gln Asn Leu Asp Tyr Tyr Gln Thr Met Ser
        180                 185                 190

Gly Val Lys Glu Ala Asp Phe Arg Asp Leu Glu Ala Lys Pro His Met
        195                 200                 205

His Glu Phe Arg Leu Gly Val Arg Leu Tyr Ser Glu Glu Lys Pro Gln
    210                 215                 220

Glu Ala Val Pro His Leu Glu Ala Ala Leu Gln Glu Tyr Phe Val Ala
225                 230                 235                 240

Asp Glu Glu Cys Arg Ala Leu Cys Glu Gly Pro Tyr Asp Tyr Asp Gly
                245                 250                 255

Tyr Asn Tyr Leu Asp Tyr Ser Ala Asp Leu Phe Gln Ala Ile Thr Asp
        260                 265                 270

His Tyr Val Gln Val Leu Asn Cys Lys Gln Asn Cys Val Thr Glu Leu
        275                 280                 285

Ala Ser His Pro Ser Arg Glu Lys Pro Phe Glu Asp Phe Leu Pro Ser
    290                 295                 300

His Tyr Asn Tyr Leu Gln Phe Ala Tyr Tyr Asn Ile Gly Asn Tyr Thr
305                 310                 315                 320

Gln Ala Ile Glu Cys Ala Lys Thr Tyr Leu Leu Phe Phe Pro Asn Asp
                325                 330                 335

Glu Val Met His Gln Asn Leu Ala Tyr Tyr Thr Ala Met Leu Gly Glu
        340                 345                 350

Glu Glu Ala Ser Ser Ile Ser Pro Arg Glu Asn Ala Glu Glu Tyr Arg
        355                 360                 365

Arg Pro Asn Leu Leu Glu Lys Glu Leu Leu Phe Phe Ala Tyr Asp Ile
    370                 375                 380

Phe Gly Ile Pro Phe Val Asp Pro Asp Ser Trp Thr Pro Glu Glu Val
385                 390                 395                 400

Ile Pro Lys Arg Leu Gln Glu Lys Gln Lys Ser Glu Arg Glu Thr Ala
                405                 410                 415

Val Arg Ile Ser Gln Glu Ile Gly Asn Leu Met Lys Glu Ile Glu Thr
        420                 425                 430

Leu Val Glu Glu Lys Thr Lys Ser Leu Asp Val Ser Arg Leu Thr
        435                 440                 445

Arg Glu Gly Gly Pro Leu Leu Tyr Glu Gly Ile Ser Leu Thr Met Asn
    450                 455                 460

Ser Lys Val Leu Asn Gly Ser Gln Arg Val Val Met Asp Gly Val Ile
465                 470                 475                 480

Ser Asp Asp Glu Cys Gln Glu Leu Gln Arg Leu Thr Asn Ala Ala Ala
                485                 490                 495

Thr Ser Gly Asp Gly Tyr Arg Gly Gln Thr Ser Pro His Thr Pro Asn
        500                 505                 510
```

```
Glu Lys Phe Tyr Gly Val Thr Val Leu Lys Ala Leu Lys Leu Gly Gln
        515                 520                 525

Glu Gly Lys Val Pro Leu Gln Ser Ala Arg Thr Ala Leu Gln
        530                 535                 540

<210> SEQ ID NO 9
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 9
ggatccaagg agcgggctct gcgctcgc                                         28

<210> SEQ ID NO 10
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 10
ccaagcttgg ctgtgtaata a                                                21

<210> SEQ ID NO 11
<211> LENGTH: 19
<212> TYPE: DNA
<213> ORGANISM: Artificial Sequence
<220> FEATURE:
<223> OTHER INFORMATION: Artificially Synthesized Primer Sequence

<400> SEQUENCE: 11
tcattacatc caggtcctc                                                   19

<210> SEQ ID NO 12
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 12
tttggagttc atggtgagac                                                  20

<210> SEQ ID NO 13
<211> LENGTH: 38
<212> TYPE: DNA
<213> ORGANISM: Artificial Sequence
<220> FEATURE:
<223> OTHER INFORMATION: Artificially Synthesized Primer Sequence

<400> SEQUENCE: 13
agatctagat ctatggcggt acgcgcgttg aagctgct                              38

<210> SEQ ID NO 14
<211> LENGTH: 39
<212> TYPE: DNA
<213> ORGANISM: Artificial Sequence
<220> FEATURE:
<223> OTHER INFORMATION: Artificially Synthesized Primer Sequence

<400> SEQUENCE: 14
gtcgacgtcg acttcatagc tcatccttgg gcttcgatt                             39
```

```
<210> SEQ ID NO 15
<211> LENGTH: 40
<212> TYPE: DNA
<213> ORGANISM: Artificial Sequence
<220> FEATURE:
<223> OTHER INFORMATION: Artificially Synthesized Primer Sequence

<400> SEQUENCE: 15
gtcgacgtcg actctaggtg ccctgctcac gggggccgat                             40
```